United States Patent [19]
Spinello

[11] Patent Number: 5,401,444
[45] Date of Patent: * Mar. 28, 1995

[54] APPARATUS AND METHOD FOR VERIFIABLY STERILIZING, DESTROYING AND ENCAPSULATING REGULATED MEDICAL WASTES

[75] Inventor: Ronald P. Spinello, Westbury, N.Y.

[73] Assignee: Spintech Inc., York, Pa.

[*] Notice: The portion of the term of this patent subsequent to Jan. 7, 2009 has been disclaimed.

[21] Appl. No.: 32,961

[22] Filed: Mar. 18, 1993

Related U.S. Application Data

[63] Continuation-in-part of Ser. No. 817,475, Jan. 3, 1992, abandoned, which is a continuation-in-part of Ser. No. 531,943, Jun. 1, 1990, Pat. No. 5,078,924, which is a continuation of Ser. No. 364,978, Jun. 9, 1989, Pat. No. 4,992,217.

[51] Int. Cl.⁶ ............................................. A61L 11/00
[52] U.S. Cl. ................................ 264/0.5; 422/294; 422/307; 588/215
[58] Field of Search .................... 264/0.5; 252/628; 422/294, 307, 255, 358, 1; 427/331; 523/129

[56] References Cited

U.S. PATENT DOCUMENTS

| | | | |
|---|---|---|---|
| 3,476,506 | 11/1969 | Andersen et al. | 422/294 |
| 3,892,706 | 7/1975 | Jetzer | 523/129 |
| 4,409,029 | 10/1983 | Larker et al. | 264/0.5 |
| 4,434,074 | 2/1984 | Fox et al. | 252/628 |
| 4,552,720 | 11/1985 | Baker et al. | 422/26 |
| 4,662,516 | 4/1987 | Baker, Sr. et al. | 206/363 |
| 4,756,681 | 7/1988 | Unger et al. | 264/0.5 |
| 4,834,917 | 5/1989 | Ramm et al. | 252/628 |
| 4,860,958 | 8/1989 | Yerman | 241/23 |
| 4,992,217 | 2/1991 | Spinello | 252/628 |
| 5,078,924 | 1/1992 | Spinello | 264/0.5 |

Primary Examiner—J. Woodrow Eldred
Attorney, Agent, or Firm—Hoffmann & Baron

[57] ABSTRACT

Apparatus and method for processing regulated medical waste using a processing oven having multiple temperature ranges and compacting means and an oven with means for sensing and generating heat near the base of the medical waste container. Temperature-calibrated thermoplastic engineered to liquefy at temperatures assuring sterilization of biological contaminants within the time frame of liquefaction and re-solidification is formed into a waste-receiving hopper capable of withstanding waste compaction pressures prior to liquefaction and compaction states are performed both before and after liquefaction. Self-lidding thermoplastic containers utilize the mass of thermoplastic covers, or other forces, to consolidate the mass. A laminate is applied to the container to control plastic flow during liquefaction.

19 Claims, 15 Drawing Sheets

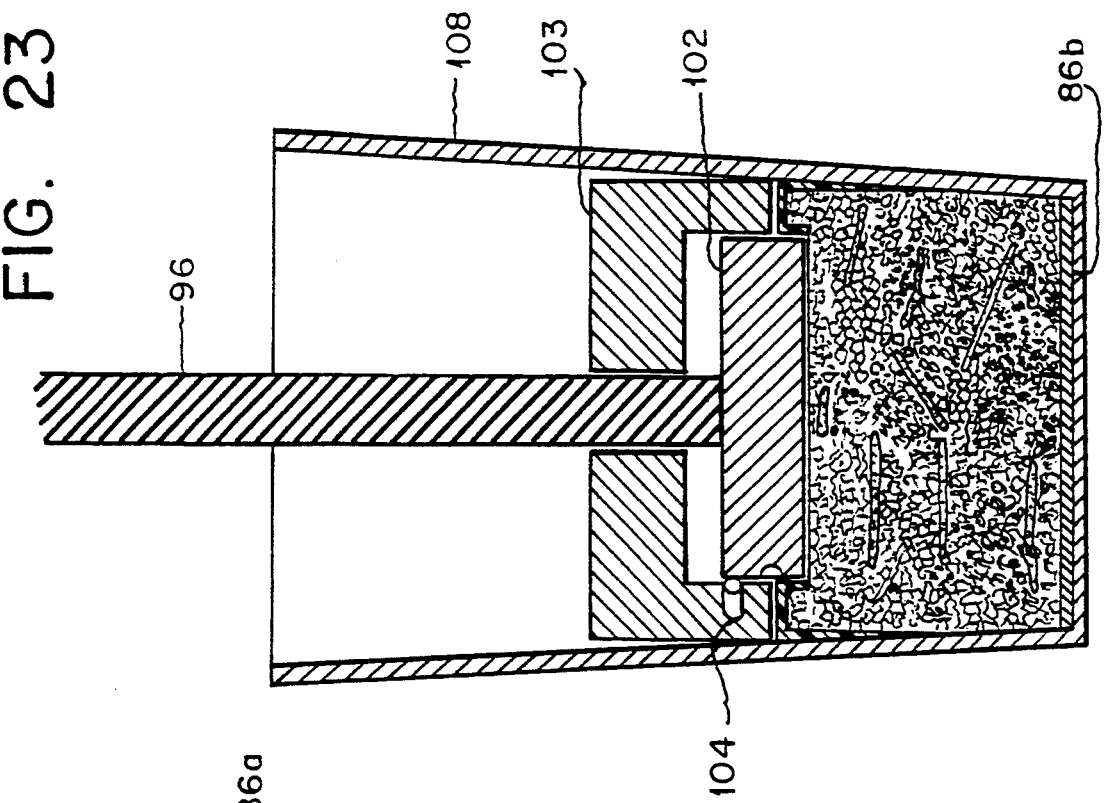
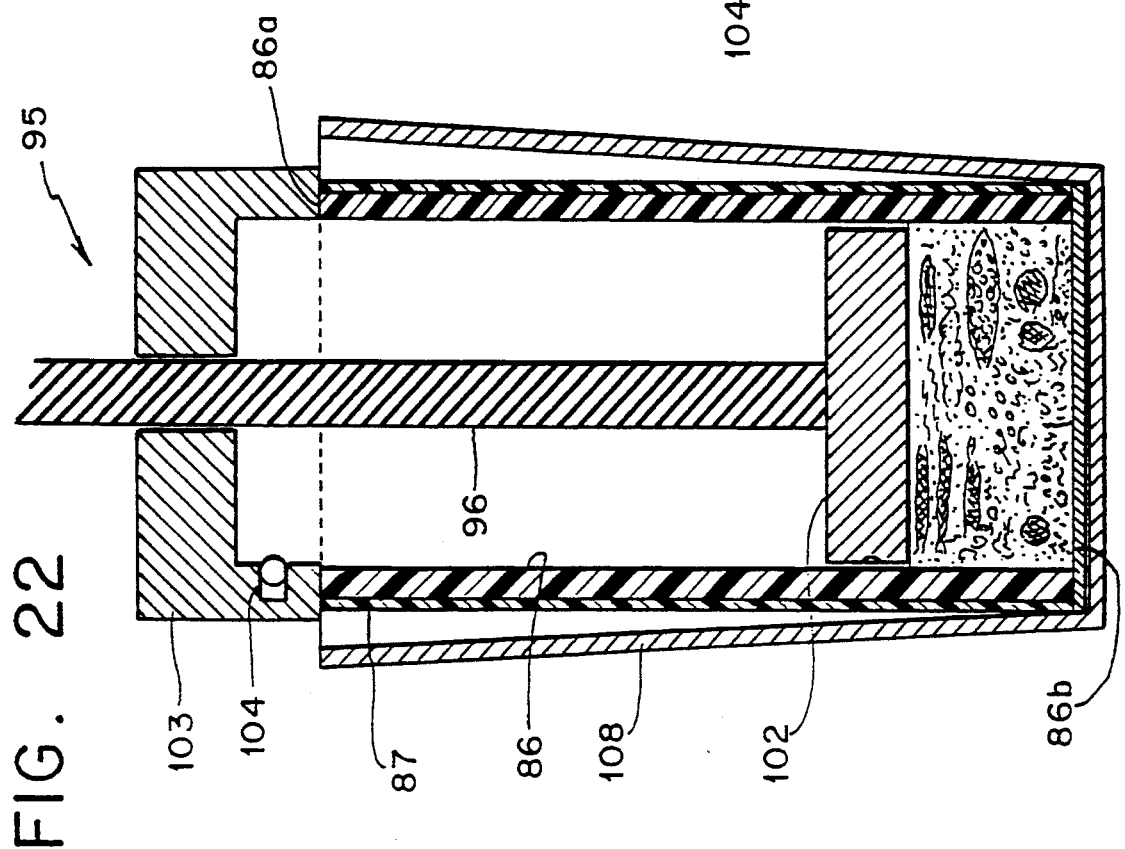

APPARATUS AND METHOD FOR VERIFIABLY STERILIZING, DESTROYING AND ENCAPSULATING REGULATED MEDICAL WASTES

RELATED APPLICATIONS

This is a continuation in part of the Applicant's application Ser. No. 07/817,475, filed Jan. 3, 1992, to be abandoned, and which is a continuation in part of application Ser. No. 07/531,943, filed Jun. 1, 1990, now U.S. Pat. No. 5,078,924, which is a continuation of application Ser. No. 07/364,978, filed Jun. 9, 1989, now U.S. Pat. No. 4,992,217.

The invention is directed to safe handling and disposal of regulated medical waste such as medical implement waste from hospitals, health care facilities and dental and medical offices. It is particularly concerned with safely processing contaminated needles, scalpels, and like sharp metal or glass objects which have invaded the human body, as well as used thermoplastic hypodermic syringes, tubing, vials of glass or plastic and containers which have been in contact with body fluids, all of which are difficult and dangerous to handle, destroy or eventually store.

BACKGROUND OF THE INVENTION

Environmental protection laws at all levels of government are concerned with contaminated medical wastes also now known as regulated medical wastes. In most jurisdictions of the civilized world, such wastes can no longer be put into the conventional channels of waste disposal. Nor can much of such wastes be reliably rendered safe and unrecognizable in a practical, discernible way at the point of use. On-site sterilization, by autoclaving, for example, of medical waste does not solve the problem because sterilization is not only labor-intensive, but subject to human error and all but impossible to verify. Also, sterilizing does not change the inherently dangerous character of sharps such as needles and scalpels, nor does it render syringe bodies unrecognizable or unusable.

Used thermoplastic hypodermic syringes are possibly the most dreaded waste of all because they are contaminated, dangerous to handle, resist decay, can float until a shore is found, and, as operative devices, are sought by the illicit drug trade. Until recently, medical facilities were required to shear off the needle part from the syringe body immediately after the injection, but this procedure was found to spread disease by means of the air-borne aerosols generated by the mechanical shearing action. Also, both the contaminated needle tip and syringe body remained to be handled and disposed of as regulated waste. Current regulations call for dropping the contaminated syringe with needle intact into a safe container, called a "sharps" box, for custom delivery to an authorized repository in a costly and dubious process known as tracking.

A state-of-the-art device destroys the needle at the point of use by passing a large current at low voltage through the needle to reduce it and all attendant contaminants at temperatures of incandescence to a minute, sterile, incinerated residue. That invention protects the nearby medical personnel and the environment but it cannot cope with scalpels, glass or the leftover hollow barrels of the syringes. Thus, the medical facility, while performing a useful service to protect its personnel and society, is left with its other contaminated "sharps" and syringe bodies to ship to a safe repository. For its otherwise worthwhile efforts, it has saved little time and little, if any, total disposal cost.

There are also in the prior art techniques for rendering sharp items less dangerous by potting in gels, hardenable resins or thermoplastics. U.S. Pat. No. 4,662,516 to Baker Sr. et al., discloses a sharps waste collection box and an unverifiable sterilizing cycle in which the wastes are first caught in a thermoplastic bag containing supplemental thermoplastic panels and then placed in an autoclave to be processed through a conventional autoclaving cycle, i.e. steam under pressure for a timed interval, typically 20–30 minutes at approximately 120° C. The plastic bag and panels are shown to have melted at the autoclave temperature and are shown encapsulating at least to some extent the medical waste (a hypodermic syringe barrel and needle).

The finished product, however, remains hazardous by all applicable definitions and must therefore be handled as if it had never been treated. First, the treated waste is recognizable. Much of today's medical wastes, such as glass vials, hollow syringe needles and barrels in particular, can be buoyant in liquefied plastic; needles can in the absence of constraint project from the solidified mass making them not only recognizable but exposed and legally regulatable (even if actually sterile). The treated waste, however, is not sterile. Autoclave sterilization depends on "wet" heat reaching all microbial life for a finite period of time; shielding the waste in a plastic bag or immersing it in liquefied plastic hampers the wet or autoclave process. Thus, even more time and higher temperatures would be indicated if sterilization were to be achieved. But more important, sterilization even if performed to all applicable standards is simply not verifiable on casual (or even less casual) inspection and better, safer solutions are sought.

The present regulations for dealing with medical instrument wastes call for: 1) minimum handling at the point of use, that is the person performing the injection, for example, is expected to drop the used syringe directly into the "sharps" box; 2) containerizing the waste by means of sealed and clearly marked and regulated waste containers, and 3) either destroying on the site by licensed incineration or logging and shipping the containerized, contaminated waste to a special repository (typically a special state-of-the-art incineration station) under an umbrella of costly manifests which must circulate among the facility, the hauler and the repository and then kept available for audit for several years. The expense of this tracking procedure to society is enormous and the beaches and land fills of the world reveal the flaws in the system.

The present invention is a fresh attempt to solve the problems. Its objects and features are:

to provide a relatively inexpensive waste disposal container to receive the medical waste at the point of use;

to provide a way to process and sterilize inexpensively and verifiably the contaminated contents within the container while still at the medical facility;

to render the syringe bodies in the container not only unusable but unidentifiable, and unretrievable;

to render the needles, the scalpels and the glass harmless against cutting or piercing personnel and to render them unrecoverable by any practical means;

to provide a containerized sterilizing system which is reliable and virtually immune to human error;

to provide a containerized sterilizing system which provides a biological indicator even to the casual observer whether the contents have been rendered harmless and safe;

to provide a containerized medical implement waste disposal system in which the treated container and its contents do not float;

to provide a reliable, relatively inexpensive method and apparatus to pretreat partial loads of medical wastes at the point of use on a day-by-day or even on-demand basis in a manner which renders the contents unusable and at least partially sterile and followed by a final sterilizing and encapsulating cycle to yield a product which can be thrown out in the ordinary channels of waste disposal; and to provide a containerized sterilizing system for medical implement waste which, if desired, lends itself to recycling.

BRIEF SUMMARY OF THE INVENTION

In accordance with the invention, a waste disposal container which can be similar in size and shape to existing "sharps" boxes is formed of a material such as metal or engineered plastic having a melting point exceeding conventional sterilization temperatures. The container includes a temperature-calibrated or indexed-thermoplastic compound preferably having a melting temperature selected at a value at which sterilization of biological contamination is effected virtually upon contact. Used medical implement and general waste such as hypodermic needles, scalpels, tongue depressors, glass vials, tubing and hypodermic syringes, with or without the needles, as well as blood soaked gauze, extracted teeth or the like are accumulated in the container in the conventional manner. The full container is heated by appropriate means such as an oven to a temperature at or above the melting point of the temperature-calibrated compound. When the compound liquefies, pressure is applied by a movable member to cause the hot liquid to flow into the space containing the then pre-heated waste products, to flow over and around all bits and pieces, and to fill substantially all void spaces between and in the waste items. The container is vented at the top and the flow continued preferably until the liquefied compound appears at or around the movable member. All biological life will then, or shortly thereafter, be killed as the liquid hardens with attendant heat of fusion effects.

In one embodiment, the container is partially collapsible to apply pressure. Alternatively, the container can be formed of telescoping parts. It is this feature which provides an error-free, highly conspicuous and verifiable indication that the sterilizing and encapsulating steps have occurred within. The pressure and containment of the compressed container forces all waste into the molten material and molten material into the void spaces. If desired, the outside of the container can be color and word coded to show the hazardous mode before the container is reduced in size and the safe mode thereafter.

The container is held in its new geometry until the compound has cooled and hardened to encapsulate and shield all sharp points and edges and to lock the container in its new geometry. The plastic of which disposable syringe bodies are made, having a melting temperature substantially below that of the compound, will be reduced to an amorphous, unrecognizable, void-free mass. Thus, there are no visually identifiable or usable syringe parts remaining in the final mass. The container is now hazard-free and can be disposed of in the conventional channels of waste disposal either at a land fill or an incinerator. It is also capable of recycling to retrieve the compound and the metals of which the medical implements were made, should such be desirable for any reason.

In another preferred embodiment of the invention, two or more differently temperature-calibrated (high and low) media can be used in the waste disposal container to effect economies of space and capacity and to make it possible to pre-treat and render at least partially safe a plurality of successive small loadings of hazardous waste on a day-by-day or even hour-by-hour basis. As above, the container is locked in its full open, hazard-indicating geometry by a volume of high or sterilizing temperature medium. Additional low melting point medium can be embodied in the inside container design or added as a supplement in the form of loose material, secondary plastic sharps containers or by plastic medical waste items per se.

Design considerations are discussed in greater detail below but in brief medical waste items which are non-meltable and non-compressible such as glass anesthetic and blood vials, extracted teeth and metal implements are at one end of the displacement spectrum and meltable and compressible items such as plastic syringe barrels, flexible tubing, sharps boxes and blood soaked gauze are at the other. The invention addresses both extremes and the gamut of combinations.

In the previously described embodiments, a fully waste-loaded container calls for a finishing and sterilizing cycle which ends the processing life of the basic medical waste disposal container. In this embodiment, the two differently temperature-calibrated plastic media matched by a companion oven having two processing temperatures enables initial full charges of waste to be preliminarily processed reducing their volume significantly (with substantial safety benefits) without triggering the final action. Successive loadings, although progressively smaller in volume, materially augment the total capacity of each processing container, e.g. a 100 fl. oz. capacity container can process up to approximately 400 fl. oz. (displacement) of meltable compressibles and up to 200 fl. oz. of non-compressibles; the cost savings are substantial.

The pre-processed materials will be rendered unrecognizable, unspillable, essentially unusable, substantially free of biologically active materials (and therefore odor-free) and, to a very large extent, sterile. But for the projecting sharps or hazards, all disposed, however, within the closed container (preferably also housed within its oven) and but for resistant spores, the intermediate or preliminary treatment has rendered the waste safe. Smaller charges of known highly dangerous waste can be immediately processed at any time and a day's collection can be processed even if less than a full charge, all without triggering the final sterilizing step which necessarily ends the useful life of the waste-processing container.

When, however, the container does reach its ultimate capacity which can be either visually or mechanically signalled to the waste generating facility, the final sterilizing and finishing stage with an oven-temperature of say 190° C. or above is initiated. The mass is rendered totally biologically inert, all projecting needles (hazards) within the container are submerged by compression, there are no recognizable or re-usable, elements and the container reverts from its hazard-indicating mode (by warning indicia on a surface) to non-hazardous in every way (including obliterating the warning indicia) for disposal in the regular waste channels. In accordance with the invention, supplemental forces can be applied by the oven to assist in the compression stage and various safety interlocks, automatic cycling and load weighing features can be added to the oven and container functions.

In still another embodiment of the invention economies of space, energy, supplemental plastic and container costs are achieved together with versatility in the accommodation of medical wastes having widely differing physical characteristics. A permanent heat-resistant container part is combined with an expendable or temporary hopper section preferably cylindrical and formed of temperature-calibrated plastic. The hopper has a receptacle volume that holds medical waste in its untreated states in amounts which after heat reduction in which it is united with the temperature calibrated plastic will form a solid, void-free sterile structure. Processing by heat is supplemented by relatively strong compression steps which can occur not only during or just after melt-down (as in other disclosed embodiments) but prior to melt-down to effect preliminary volumetric reductions, re-orient randomly projecting needles into more harmless attitudes and to break glass vials and the like which consume space wastefully. Such preliminary processing, preferably conducted in the presence of some heat by a selectively operable oven thermostat is also conducive to creating a container system which is self-lidding. With upwardly projecting needles preferably pre-pressed horizontally the temperature-calibrated plastic can be caused to flow over (as well as into) the waste load during and subsequent to melt-down to form when solidified an imperforate permanently affixed cover on the container. If desired compression forces can be brought to bear in the final stages to contour and control the lidding process. Other heat resistant laminations in the form of foil, film or latex coatings can be applied to the temperature calibrated thermoplastic of the hopper to control the geometry of the melt-down process and to avoid problems of plastic adhering to the compression elements and other oven parts.

In another embodiment of the invention the temperature-calibrated plastic container can be made self-lidding and can provide its own low level compacting pressures by providing a relatively massive thermoplastic lid and processing the unit in an oven-processor which is selective in its application of heat to cause the container to liquefy from the bottom thus slowly immersing the waste in sterilizing and encapsulating plastic. The heavy lid slowly lowers itself and the molten mass and into the vicinity of the heat where it melts onto the mass to provide a covering over all upwardly projecting sharps.

BRIEF DESCRIPTION OF THE DRAWINGS

FIGS. 22 and 23 are side views in vertical section illustrating the two compaction cycles performed by the oven of FIGS. 19 and also the self-lidding feature of the container assemblies;

DESCRIPTION OF THE PREFERRED EMBODIMENTS

Figure 1:
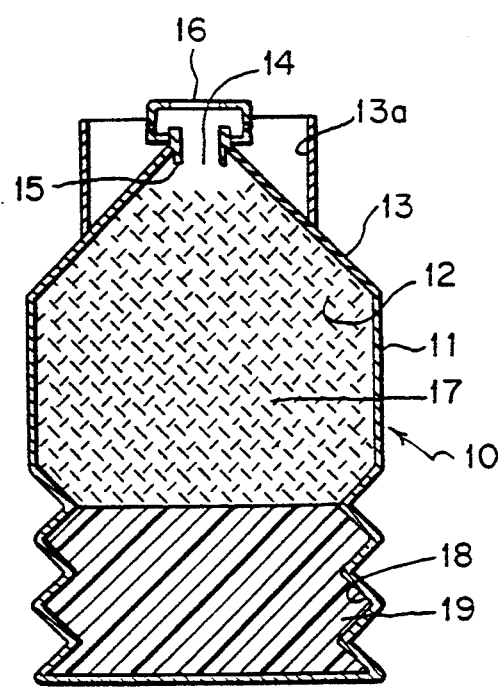
FIG. 1 is a view in side view in vertical section of a waste container formed in accordance with the invention holding a charge of medical waste prior to the sterilization and encapsulating steps.
Figure 2:
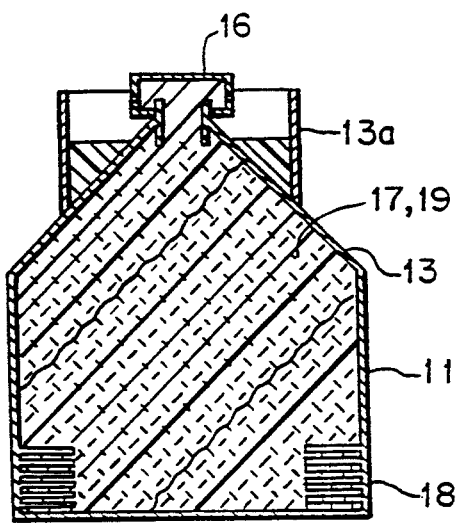
FIG. 2 is a view in side view in vertical section corresponding to FIG. 1 after the sterilizing and encapsulating steps.

Referring to FIGS. 1-4, the invention is illustrated as embodied in a container 10 formed of a heat and puncture resistant material such as engineered high melting point plastic, of which nylon and teflon are examples and which can be reinforced, or of metal. The container 10 is cylindrical and includes a rigid upper portion 11 defining a chamber or space 12 to receive waste implements such as hypodermic needles, glass vials, scalpels, extracted teeth and like waste products which in the medical and dental professions are now known as contaminated "sharps". Syringe bodies, with or without the needles attached, flexible tubing and needle hubs can also be included, such typically being of the single-use, disposable type formed of thermoplastic. Such thermoplastics typically melt at temperatures of approximately 150° C. more or less so that all thermoplastic waste items will be melted down and rendered unusable, unretrievable and unrecognizable. The upper portion 13 of the container is preferably convergent to form a relatively small waste-receiving opening 14 having a depending cylindrical wall 15 and closed by a detachable vented cap 16.

The lower or base portion of the container comprises a collapsible storage space 18 containing a thermoplastic medium 19 which is temperature calibrated as to its melting point selected to achieve sterilization of all known biological micro-organisms including vegetative bacteria, viruses and spore forms. A typical material for this purpose which is relatively harmless to the environment is linear, hydroxy terminated copolyester synthetic resin which can be formulated to afford full flow viscosity at temperatures from 160° C. to in excess of 260° C. Such products do not vaporize or generate toxic fumes until temperature in excess of 300° C. are reached. They are marketed for other purposes under such trademarks as Dynapol and Jet-Melt. Many acrylics and polypropylenes can also be adapted for the purpose.

Most medical researchers studying the effects of heat as a means of sterilizing refer to a temperature coefficient model in which death of the micro-organisms being studied (death time) is plotted as a function of time and temperature. Research strongly indicates that no known micro-organisms can survive temperatures in excess of 160° to 190° C. for longer than a fraction of a minute. See "Disinfection, Sterilization and Preservation", by Seymour S. Block, Lea & Febiger, 1983. It should be understood, however, that there is a given range of times and temperatures below 160° to 190° C. which effectively kill all known micro-organisms. It is, therefore, possible to design systems whereby plastics having melting temperatures less than 160° to 190° C. are allowed to remain in contact with the micro-organisms for times consistent with the death times of the organisms. The preferred embodiment, however, makes use of plastics having temperatures high enough to kill the micro-organisms substantially on contact, and, thereby, provides a fail-safe degree of overkill. Also, the system of the present invention provides an inherent time constant representing the time for the liquid phase thermoplastic to revert during cooling to its solid final phase, yielding heat of fusion without requiring a timing function subject to human error.

In dry gaseous media such as hot air having relatively lower specific heat characteristics and little moisture, either higher temperatures or measurable time constants for heat exposure come into play. In the preferred embodiments of the present invention, liquid phase contact at temperatures achieving rapid death to all biological contaminants in their most heat-resistant form, i.e. the spore form, is desirable because it eliminates the possibility of human error in the operation of the system and renders the successful operation visually discernible and, therefore, verifiable at a glance from a substantial distance, all of which are vital in policing the environment for human life-endangering contamination.

The appearance of the thermoplastic material at the vented cap will indicate that the entire space 12 has been impregnated with molten plastic. To provide for the possibility that the displacement factor of the waste items in the space 12 will have a range of values, a surplus of thermoplastic can be provided together with an overflow reservoir 13a in the form for example of a visible, open cup surrounding the cap. To accommodate a situation in which the waste items 17 only partially fill the space 12, the conical upper portion 13 can be made collapsible under pressure in the encapsulating phase as described below.

The temperature-calibrated thermoplastic medium 19 in the embodiment of FIGS. 1-4 is illustrated as solid although it can take the form of particulate matter or granules including recycled plastics. To hold the granules in place prior to melting a covering screen, a perforate cover (not shown) can be secured to the container above the material.

The wall of the base portion 18 of the container is made collapsible by corrugation or accordion pleating locked in its open position (FIGS. 1 and 3) by the solid phase of the thermoplastic medium 19 and also locked in its collapsed position (FIGS. 2 and 4) by the same medium. If it is desired to make the container self-actuating (in the presence of heat), the collapsible wall can be made resilient with its stable or rest position collapsed. To this end, a coiled tension spring (similar to the spring 37 in FIGS. 5 and 6) can be included inside or outside the container if additional force is required. Additional force can also be derived from the use of heat shrinkable plastic in the container walls either on the x or the y axis or both, or it can be derived in whole or in part by the oven.

Figure 9:
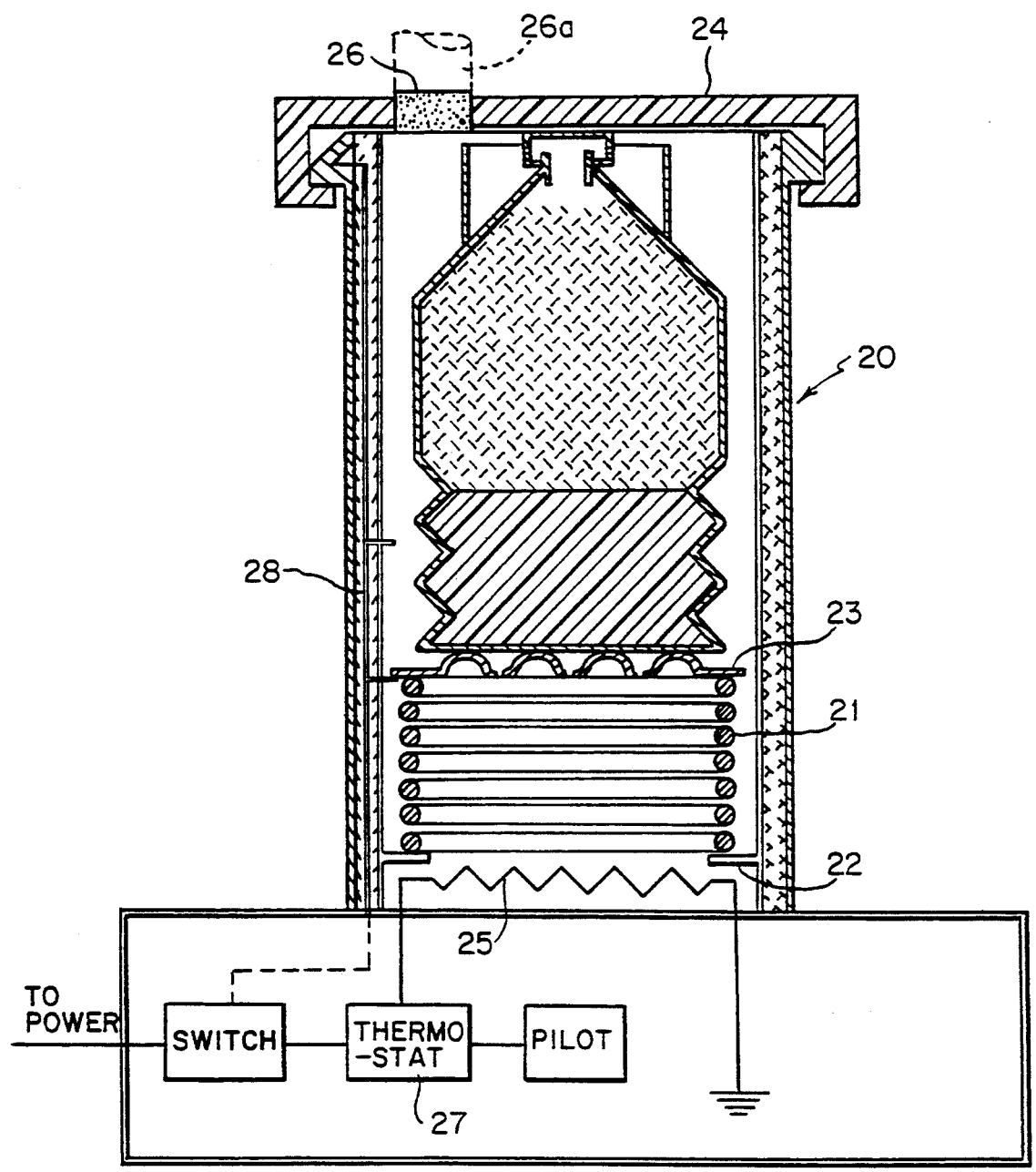
FIG. 9 is a view in vertical section of an oven containing a filled container corresponding to that of FIG. 3 and capable of carrying out the sterilizing and encapsulating functions.
Figure 10:
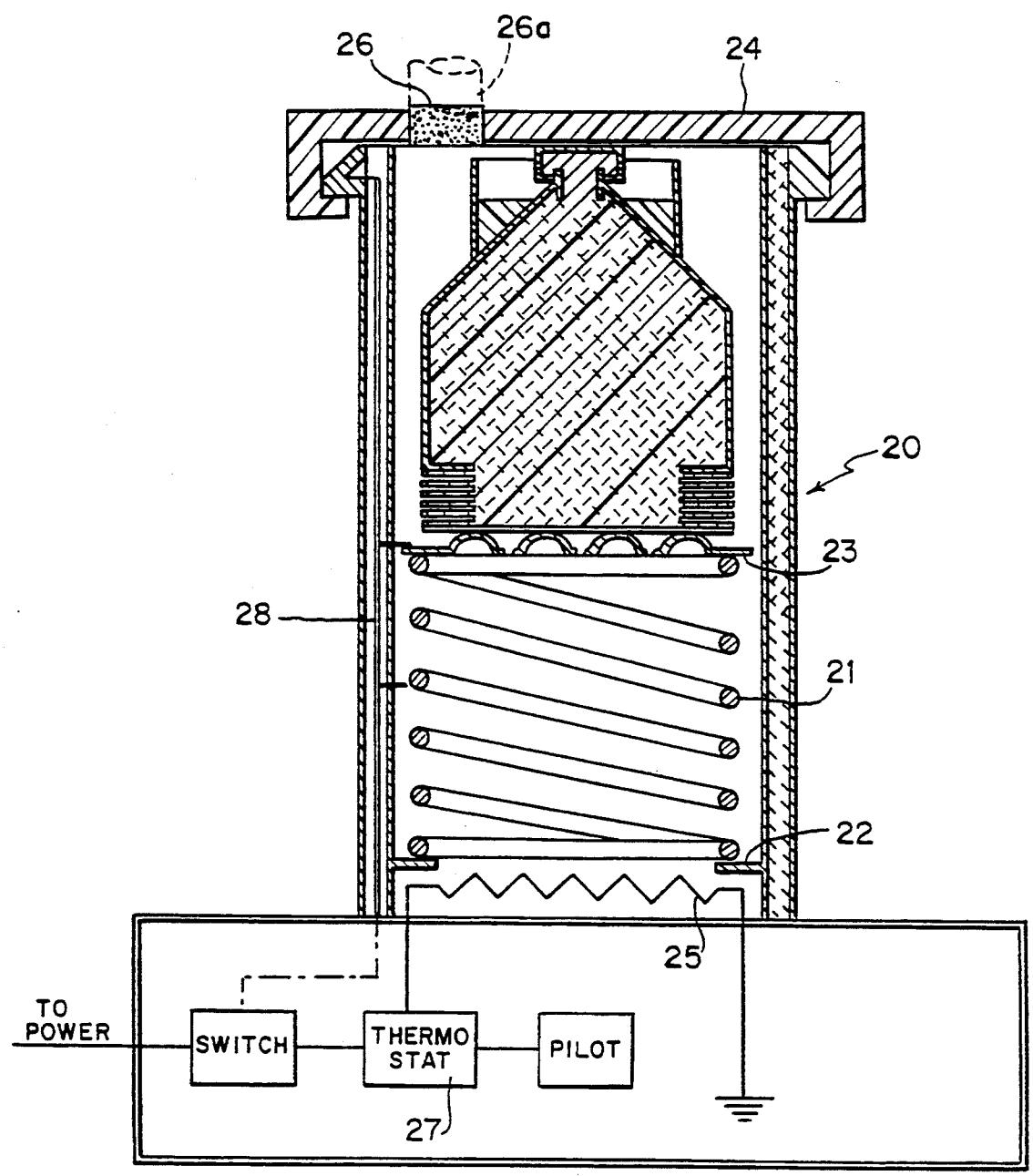
FIG. 10 is a view in vertical section of the oven corresponding to FIG. 9 but showing the container after sterilization and encapsulation.

The sterilizing and encapsulating actions in the illustrated embodiment are carried out by a special oven 20 shown in FIGS. 9 and 10 which provides forces necessary to compress the container. The oven 20 includes a compression spring 21 resting on a support 22 and carrying a perforated, corrugated plate 23 on which the filled container 10 (FIGS. 1 and 3) is seated. The spring 21 is compressed by the closed oven cover 24 pressing down on the container cap 16. A resistance heater 25 energized from the mains through a switch and thermostat 27 provides the controlled heat to liquefy the temperature-calibrated thermoplastic mass 19. As heat is applied, below the level to harm the container and above the level to liquefy the thermoplastic, melting will gradually occur at which time the liquefied thermoplastic at a temperature pre-selected to destroy the biological contaminants in the waste items 17 will begin to flow into the interstices around the preheated bits and pieces of waste in the space 12.

The biological contaminants are destroyed substantially upon contact and all sharp edges and points become encapsulated. Also, the collapsible bottom 18 of the container will compress, thereby changing the geometry and appearance of the container. Gaseous byproducts vent from the cap 16 and through a suitable filter 26, including charcoal, for example, in the cover 24 of the oven and, if desired, an evacuation conduit 26a. Alternatively, or in addition, the oven can be vented to the outside air, as is conventional in autoclave operation. The cooled container is thus rendered hazard-free and can be discarded in the conventional channels of commerce by conventional carriers. Thermoplastic syringe bodies in the container melt at temperatures below the calibrated temperature and are, therefore, melted down and destroyed as an unusable, irretrievable, unrecognizable part of the sterile, amorphous mass.

The oven 20 can be operated by a position sensing switch actuator 28 which is activated by the carrier plate 23 to initiate heating when the plate is lowered and to terminate heating when it lifts (FIGS. 9 and 10). The actuator can also be coupled to the cover 24 to release a latch when the heating cycle is completed. The cover can be spring biased to an open position when released to hurry the cooling cycle, and residual compression in the spring 21 can expose more of the container to the atmosphere and also position it to be more easily manually removed.

Figure 3:
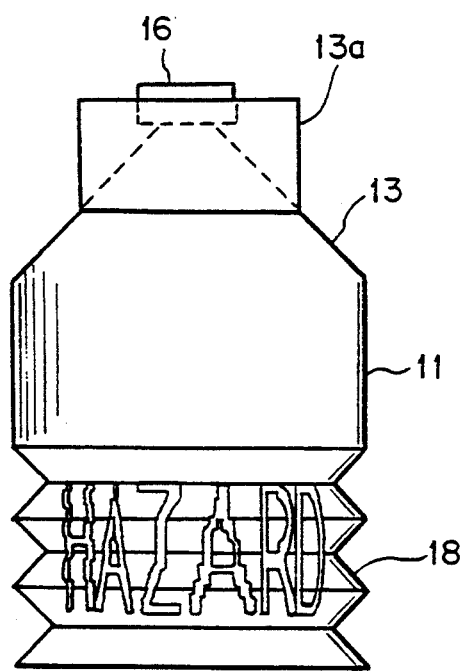
FIG. 3 is a view in side elevation of the waste container shown in FIG. 1.
Figure 4:
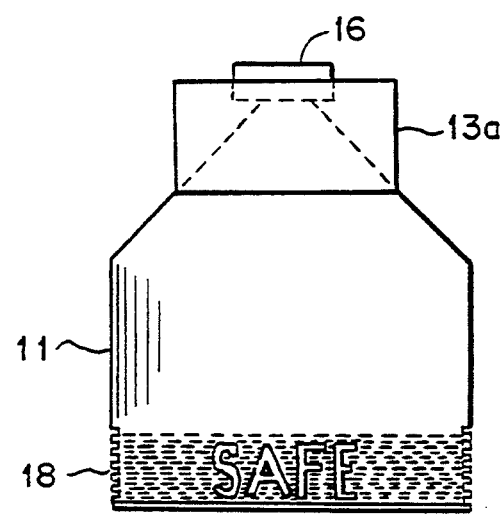
FIG. 4 is a view in side elevation of the waste container shown in FIG. 2, after sterilization and encapsulation of the waste.

The thermoplastic mass, when cooled, locks the container in its compressed condition to mark its sterile non-hazardous condition. If desired, as best seen in FIGS. 3 and 4, the concave or depressed portions of the base can be color coded in red to indicate the hazardous state and a word to that effect can be included. The word "Hazard" as used in this disclosure is intended in its broader sense to mean contaminated, sharp or infected and not, for example, explosive or highly inflammable. "Regulated medical waste" is a more precise legal definition of the waste to which this invention is directed. The outer edges can be marked so that when compression has occurred the word "safe" appears and the hazard indicator disappears. Because the thermoplastic mass 19 has been selected for a melting temperature close to or above that which sterilizes on contact, the system becomes error proof and visually verifiable. It will be understood that a certain margin for error is built into the system in that a finite time factor for killing by heat is inherent in the system representing the time for cooling down to the solid phase with attendant heat of fusion. Thus, it is not essential that the temperature of the liquefied thermoplastic actually reach that which kills instantaneously, although it is preferred where possible to establish safety factors using both elevated temperatures as well as any time factor which is inherent in the time required for the temperature of the thermoplastic to drop to that at which the solid phase occurs.

Figure 5:
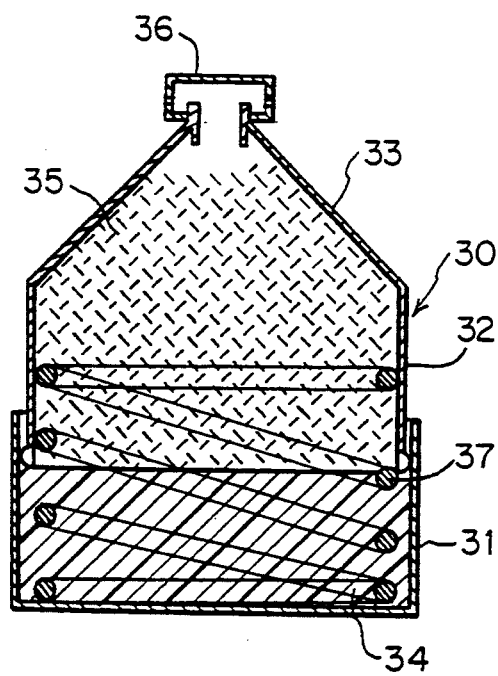
FIG. 5 is a view in vertical section of another embodiment of the invention prior to sterilization and encapsulation.
Figure 6:
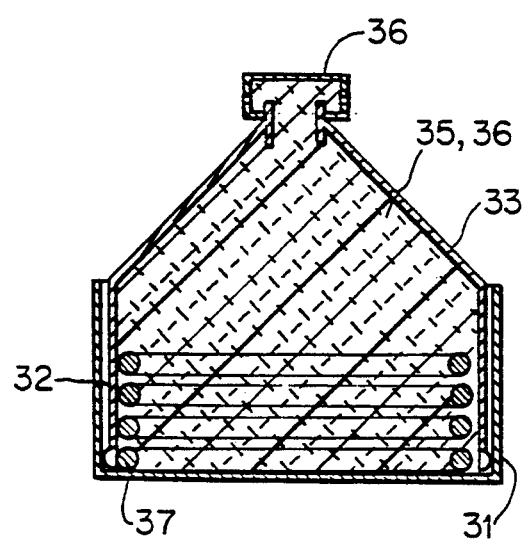
FIG. 6 is a view in side elevation of the unit of FIG. 5 after sterilization and encapsulation.

Referring to FIGS. 5 and 6 another embodiment of the container is disclosed in which the container 30 is formed of telescoping base and top sections 31 and 32, respectively. As in the embodiment of FIGS. 1–4, the upper part 33 of the top section 32 is conical. Normally solid phase thermoplastic 34 fills the base 31 with waste items 35 filling the upper section, shown closed by a vented cover 36. The thermoplastic 34 can bond the base and top sections 31 and 32 against opening to retrieve unprocessed waste items such as syringes. If desired, the two telescoping sections can be linked by a coiled tension spring 37 joined at its top to the section 32 and its bottom to the base section 31. The container is adapted to be placed in an oven similar to that of FIGS. 9 and 10 to liquefy the thermoplastic and thereby set up the sterilizing and encapsulating functions, resulting in the configuration of FIG. 6 under the spring force, gravity or a combination thereof. Hazard warnings in the cylindrical part of the upper section will, appropriately, be obscured by the lower section. It will be understood that heat destroyable warnings can also be used.

Figure 7:
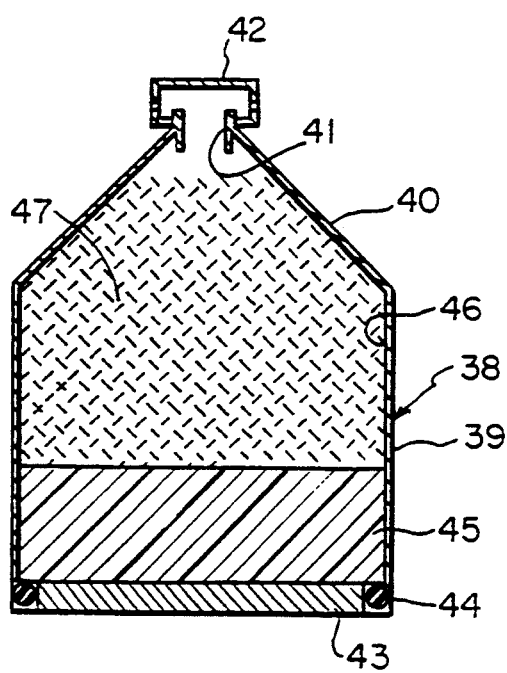
FIGS. 7 and 8 are views corresponding to FIGS. 5 and 6 of another embodiment of the invention.
Figure 8:
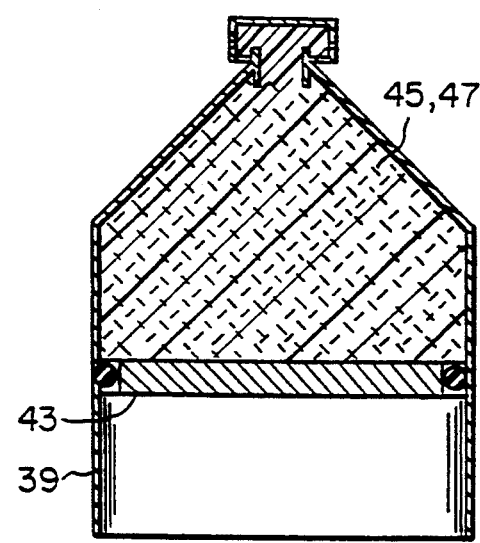

Referring to FIGS. 7 and 8 another embodiment of the invention is disclosed in which the container 38 is formed of a single piece having a cylindrical bottom 39 and conical top 40 with a filling opening 41 shown closed by a vented cover 42. The bottom portion 39 is open and has fitted thereon a piston 43 with a sealing ring 44. The bottom is filled with a volume of thermoplastic 45 of the type described above and the open space 46 above is shown filled (diagrammatically) with an array of waste items 47. A tension spring or other internal or external pressure means corresponding, for example, to the spring 37 of FIGS. 5 and 6 can be used. The filled container is then heated by, for example, an oven corresponding to that of FIGS. 9 and 10 to drive the liquefied thermoplastic into the waste items, all as described above, to achieve the end result shown in FIG. 8.

Figures 11, 12:
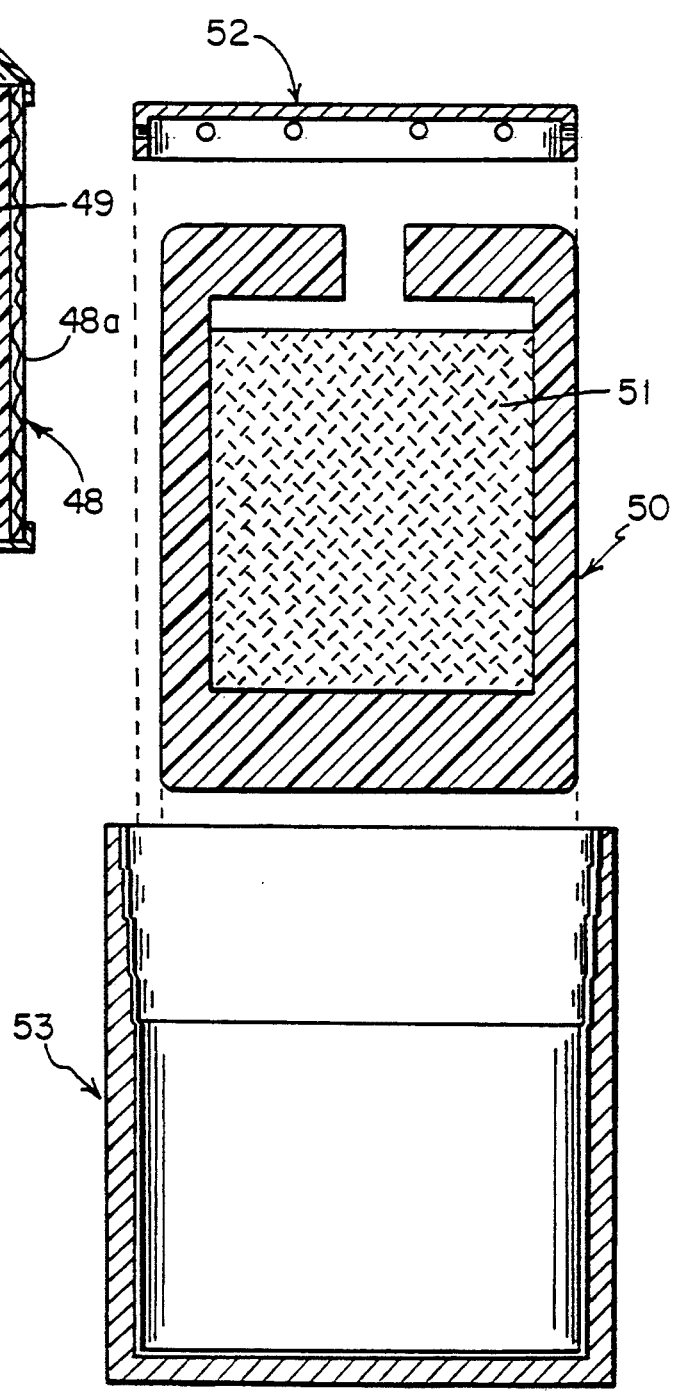
FIG. 11 is a view in vertical section of another embodiment of the invention.
FIG. 12 is a view in vertical section showing another embodiment of the invention using a separate potting container.

Another embodiment of the invention is shown in FIG. 11 in which the container 48 is itself formed of the temperature-calibrated thermoplastic resin having a wall volume corresponding to the volume required to impregnate and encapsulate the waste items 49 contained therein. The container 48 can be encased in a wrap 48a of woven or non woven filaments or of paperboard to contain and shield the liquid phase of the thermoplastic and the waste items 49. The wrap can impart deformability to the structure either in selected areas or throughout to allow the liquefied thermoplastic to be forced into the waste mass and, if desired, to adjust the container volume automatically to accommodate loads of different sizes and having different displacement characteristics. The wrap can be made puncture proof. It can also establish the pattern of change in the geometry between the treated and untreated unit to provide for the desirable visual verification of completion of sterilization.

Referring to FIG. 12 the entire sharps container 50 is formed from temperature-calibrated thermoplastic with no outer wrap or outer container. When filled with waste items 51 the container 50 with a vented cover 52, which can if desired be weighted, is dropped into a potting container 53 having tapering walls with a smooth parting surface formed for example of Teflon. The assembly is then heated in an oven to melt the thermoplastic container 50 to a sterilizing temperature of liquefaction at which time the gravity pressure causes encapsulation and impregnation of the waste items 51. When cooled and solidified the amorphous sterile mass with no projecting needles or sharps is removed from the potting container 53 for disposal as environmentally safe material via conventional disposal means.

It will be understood that while the embodiments of the invention described above utilize, as the bulk of the thermoplastic content of the containers, a temperature-calibrated thermoplastic having a melting temperature selected to achieve the desired extreme of verifiable sterilization, lower melting temperature plastic can be included within the scope of the invention to achieve additional functions. To the extent, for example, that the medical waste is itself formed of thermoplastic, such as syringe bodies, flexible tubing, scalpel handles, needle hubs and the like, lesser volumes of high temperature-calibrated thermoplastic will be required to effect total encapsulation of and therefore lack of recognition of all waste items. It is also possible to combine volumes of low and high melting temperature thermoplastic in the initial container design because the high temperature material will compel and therefore verify that the low temperature material has, in fact, while liquefied at a low temperature been raised to a temperature which is above both its actual melting and full flow liquefaction temperatures. This feature can be used to advantage to achieve in the operating container full flow (or low viscosity) characteristics in the material which can contribute to a relatively void-free structure in the finished product.

Referring to FIGS. 13–17 there are disclosed embodiments of the invention which provide maximum space utilization within the waste disposal container while providing for a large number of preliminary treatment cycles which can destroy, render unusable, and at least partially sterilize either large or small amounts of medical waste on demand. The final total-sterilization, pressure-encapsulation, and container geometry-changing cycle, all as broadly described above, can await the accumulation of waste materials approaching the theoretical maximum capacity of the container. To achieve these functions, in accordance with the invention two temperature-calibrated thermoplastic elements in the form of concentric sleeves 54 and 55 (FIG. 13) are fitted within a metal container 56. A removable cover 57 provides a large opening for depositing wastes in large or small amounts into the container, which can have a relatively large capacity, for example 100 fl. oz. of displacement (up to a month's capacity for smaller medical waste generators). Preliminary treatment significantly increases the safe working life of the unit.

The cover 57 comprises the movable compression member of the unit and includes an upstanding cylindrical center portion 58 serving as a gripping handle and providing an outer cylindrical surface 59 to carry the graphics warning of the hazardous contents. The center portion 58 can also be weighted to assist in the final compression cycle. A groove 60 can be provided for automatic gripping by an oven component for automated lifting, all as described below referring to FIGS. 16 and 17.

The melting temperatures of the two concentric sleeves 54 and 55 are critical to this embodiment of the invention, the sleeve 54 being calibrated at the high melting valve, 160° to 200° C., which gates the final desired sterilization temperature of the waste mass. The sleeve 55 is calibrated at a lower melting temperature, 110° to 150° C., to effect preliminary treatment, destruction and at least some sterilization and loss of recognition of medical wastes on demand in recurring cycles.

The volume and geometry of the high melting point plastic 54 is selected to stabilize the cover against compression movement except when the selected high temperature for final treatment is commanded by the oven. The volume of the low temperature thermoplastic 55 is selected to effect full encapsulation of the waste, obliteration of the hazard graphics, and sealing of the compression cover 57. If the waste container is to be universal in its utility it must accommodate on the one hand incompressible wastes such as glass anesthetic and blood vials, needles, scalpels, extracted teeth, and the like (which en masse, as well as individually, present void spaces) and, on the other hand, compressible and meltable wastes such as thermoplastic syringe bodies, flexible tubing, scalpel handles (which themselves undergo substantial volumetric reduction when they melt down, at the same time adding volume to the total thermoplastic mass needed in the container.

Assuming the container 56 has a capacity of 100 fl. oz., the sleeve 55 (following design criteria set forth below) would have a total displacement of 50 fl. oz. Thus, the container presents a 50 fl. oz. space (within sleeve 55) for its initial charge of wastes. Measurements show that incompressible medical wastes of the type described filling a 50 fl. oz. space contain about 25 fl. oz. of void spaces. If, therefore, the container is placed in its 2-temperature oven (FIGS. 16 and 17) and operated at the temperature required to liquefy the sleeve 55 to full flow conditions, the mass of waste will "consume" 25 fl. oz. of the plastic and thus generate more usable volume. The inside usable container space will change from a narrow cylinder to a wide cylinder as the plastic sleeve 55 melts and the impregnated mostly encapsulated waste mass will occupy the lower half of the container (ignoring for discussion purposes the thin sleeve 54) plus an additional 25%, which represents available encapsulating plastic for on-going waste loads. Successive loadings, necessarily proportionately smaller in size will eventually exhaust the system at a point approaching but typically not quite achieving theoretical maximum capacity (100 fl. oz.). Of course the preliminary treating operation can be performed at any time without the then available space having been filled, as when a particularly dangerous small waste charge is entered or when the facility closes down for the night.

Figure 13:
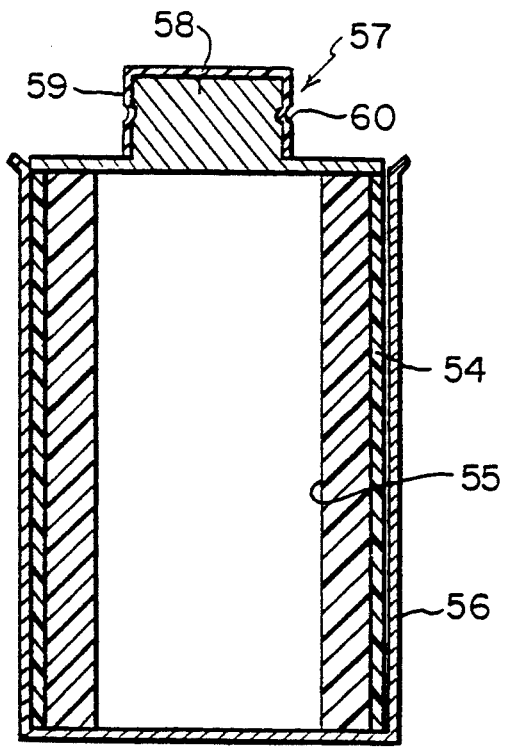
FIG. 13 is a view in vertical section showing another embodiment of the invention.

Next, consider the empty container as receiving only thermoplastic medical waste items. Measurements shows a selection of such items typically melts down to about one-forth of the space it occupies. If therefore such wastes fill the space of the container configuration as shown in FIG. 13 there will be a volume of waste consuming 50 fl. oz. of space. Melted this will reduce to about 12.5 fl. oz. of thermoplastic. In such a hypothetical case the sleeve 55 will perform no function; it is essentially for "sharps" protection. It is preferred, however, that both it and the oven be calibrated to effect the preliminary melt down at a temperature which is sufficiently high to ensure that thermoplastic medical wastes such as syringe bodies are destroyed by melting to ensure safety and economy of space. Medical thermoplastic wastes characteristically liquefy at temperatures below 140° C. It is the glass vials for anesthetics and blood (categorized as "sharps") which require the added mass of thermoplastic, whether it be of the high or low melting temperature.

Another criterion in the equation is to avoid vapor point temperatures for all thermoplastics involved, typically above 215° C. for plastic materials used in medical implements. Such vapors can be toxic, but it is possible to achieve all important objectives of the invention operating substantially below that limit.

Figure 14:
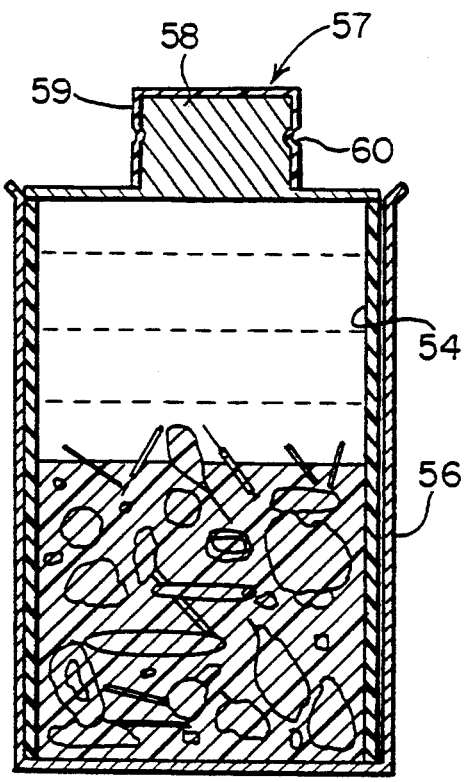
FIG. 14 is a view in vertical section of the medical waste container of FIG. 13 showing a full loading of random medical wastes pre-treated at the lower of two treating temperatures.

As stated, preliminary processing can be carried out in the unit in any number of stages until total operating capacity is approached. FIG. 14, for example, illustrates a preliminary processing of at least one full loading of medical wastes including compressible and non-compressible wastes. The dotted level lines show possible successive waste levels treated preliminarily. The sleeve 54 survives as shown.

Figure 15:
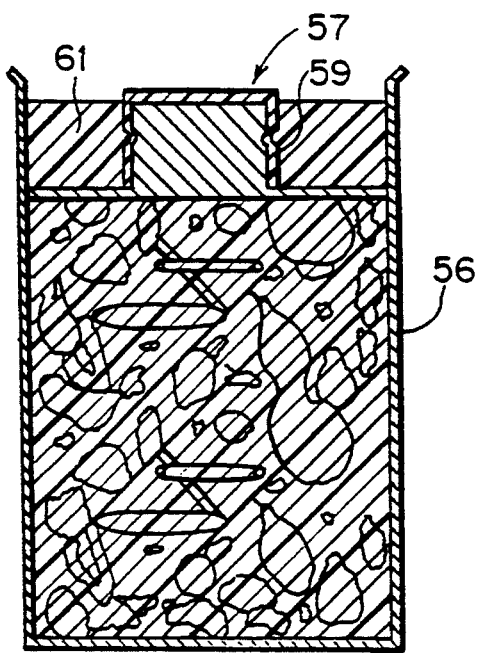
FIG. 15 is a view in vertical section showing the container after a plurality of pre-treated loadings to approximately full ultimate capacity and also after the final high temperature sterilization and compacting cycle to seal the cover portion in place over the substantially void-free structure.

FIG. 15 illustrates the effects of the final processing in which the oven has been operated at its maximum temperature to melt down the outer sleeve 54, release the compression cover 57, and submerge all non-compressible sharps hazards beneath the plastic mass (a mixture of sleeves 54–55 and the meltable thermoplastic components in the medical wastes). The cover 57 is vented by providing, for example, a small radial clearance with the wall of the metal container 56 to allow gases to escape as well as sinking of the cover into the plastic mass and the appearance of plastic in the reservoir space between the side wall 59 of the cover extension 58 and the inside of the container 56. This obliterates the hazard graphics as well as locking the cover in place. The container, fully processed, is now free of hazards, biological and mechanical, and is believed harmless to the environment and safe in all hands for final disposal in any one of several ways including, if desired, recycling through the open mail.

Figure 16:
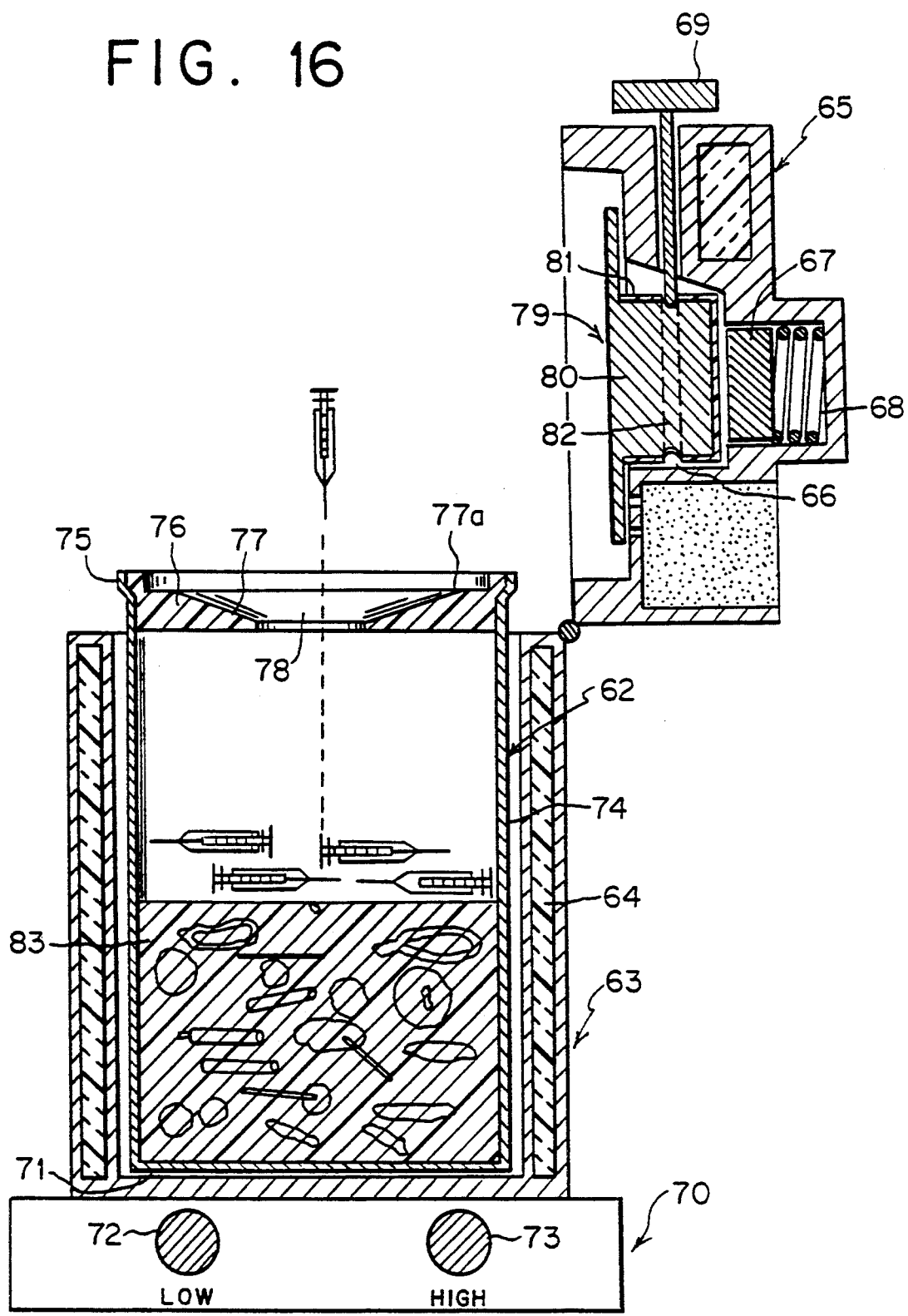
FIG. 16 is a view in vertical section of another embodiment of the invention shown in its treatment oven with its top cover carrying the removable cover of the container open to facilitate loading the container with waste items after at least one pre-treatment cycle.
Figure 17:
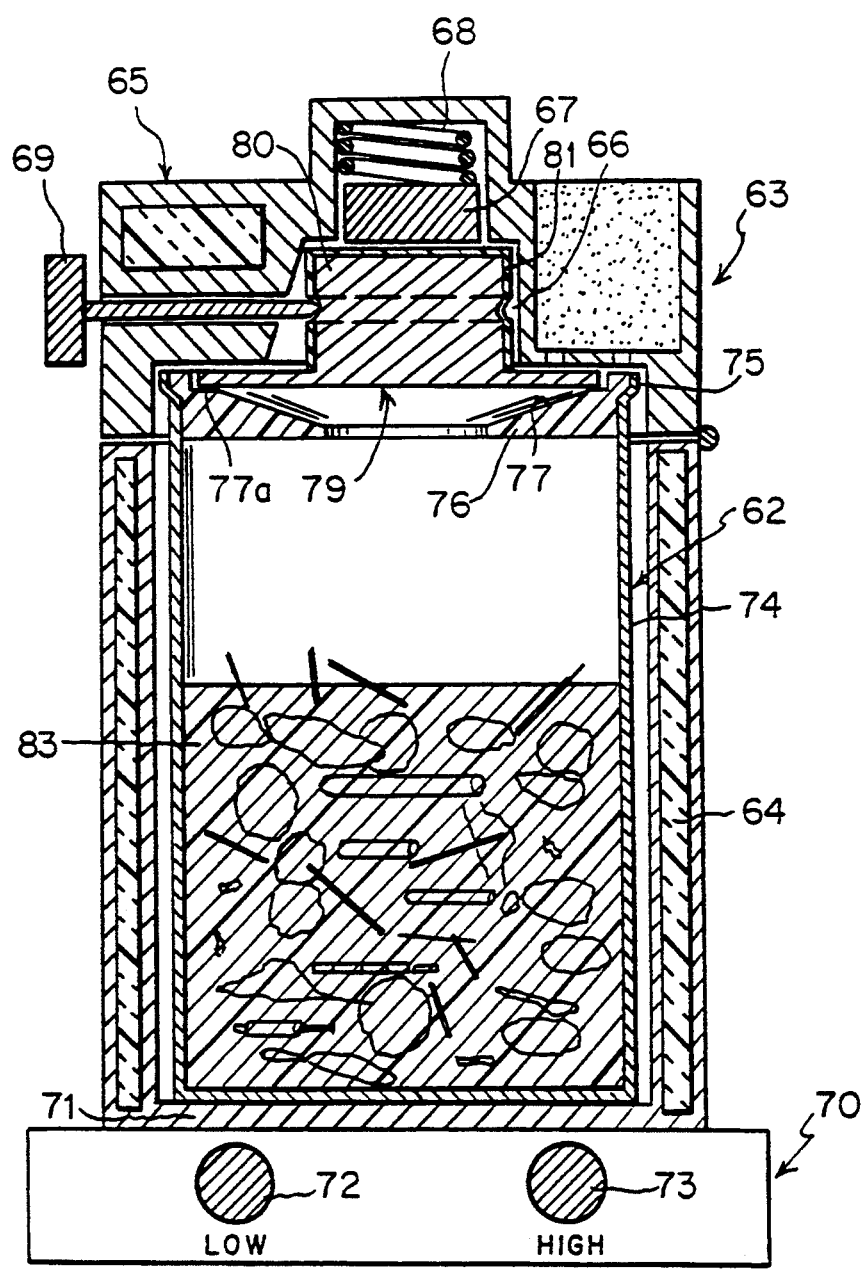
FIG. 17 is a view in vertical section corresponding to FIG. 16 but with the oven and container covers closed and after a second treatment cycle.

Referring to FIGS. 16 and 17, there is illustrated another embodiment of the invention in which the medical waste container assembly 62 is seated in a 2-temperature treatment oven 63 (shown diagrammatically) comprising an insulated cylindrical wall 64 and a hinged, insulated cover 65. The cover includes a recess 66 to receive the cover of the waste container 62, a piston 67 driven by a compression spring 68 to bear down on the cover and a spring biased automatic latch 69 to grip the cover. The oven includes a base 70 which can contain an electrically heated plate 71 having 2 relatively precision operating temperatures, the lower being in the range, for example, of 110° to 150° C. and the upper of 160° to 200° C. Manual switches 72 and 73 can be provided to operate, respectively, the low and high temperature operations for whatever predetermined time intervals are indicated, say one hour more or less per cycle. Some or all of the oven function can be automated in accordance with well known techniques and the usual assortment of safety interlocks and the like provided to discourage tampering, improper use, or excessive temperatures.

The container unit 62 includes a metal cylindrical container 74 having a contoured upper edge 75 within which is seated a contoured insert 76 formed of a temperature-calibrated thermoplastic to soften and liquefy at relatively high temperature, say 160° to 200° C. Examples of such materials have been given above. The calibrated insert 76 can include a gently downwardly conveying wall 77 to a large central opening 78 through which medical wastes can be deposited into the unit. Other geometrical configurations for the temperature-calibrated insert 76 will suggest themselves to those skilled in the art.

A unit cover 79 (corresponding to the cover 57 of FIGS. 13–15) has an outside diameter slightly smaller than the diameter of the container 74 (for venting) and normally rests within a circular ridge 77a formed on the contoured insert 76. The central, upstanding portion 80 is engaged on its upper surface by the spring biased piston in the oven lid. Hazard graphics appear on its outer wall 81 and a circular groove 82 receives the releasable latch element 69 of the oven so that when the oven door is opened the cover 79 is automatically lifted from the waste container unit 62. Disposed within the waste container is a supply of thermoplastic 83 which is calibrated to liquefy at a relatively low temperature, say 110° to 150° C.

Preliminary or low temperature processing of medical waste proceeds as described above in recurring cycles of large or small charges of waste items. When ultimate capacity is reached the cycle is changed to high temperature, at which time the contoured insert 76 of temperature-calibrated thermoplastic melts, allowing the cover 79 to drop (by a combination of its own weight and the force of the spring 68) into the container 74 to compress the heated mass, obliterate the hazard graphics, change the container geometry and lock the cover, all as described above.

It will be understood that the geometry of the calibrated low temperature plastic mass 83 has been shown in FIGS. 16 and 17 simply as a cylindrical slug of solid material. It can, of course, take other forms such as a cylindrical sleeve or it can take the form of loose granules or recycled chips. Its total volume is also subject to variation based on design and use factors. It should also be understood that because the function of the calibrated low melting temperature plastic is primarily associated with one particular type of medical waste i.e. non-compressible, non-meltable sharps of glass and metal, an alternative possible source of the supplemental thermoplastic, in accordance with the present invention, is the sub-containers in which the sharps are typically collected on the site of the waste generator. The volume of the calibrated thermoplastic used in fabricating the container (either by means of a special insert or by means of wall thickness) is keyed to the sharps capacity of the sub-container to provide an approximately correct amount to fill the void spaces and encapsulate the waste in the waste treatment container. In such event the entire filled sub-container, a sharps box in itself, is simply thrown into the waste container for preliminary processing, as opposed to being emptied into the waste process unit.

Figure 18A:
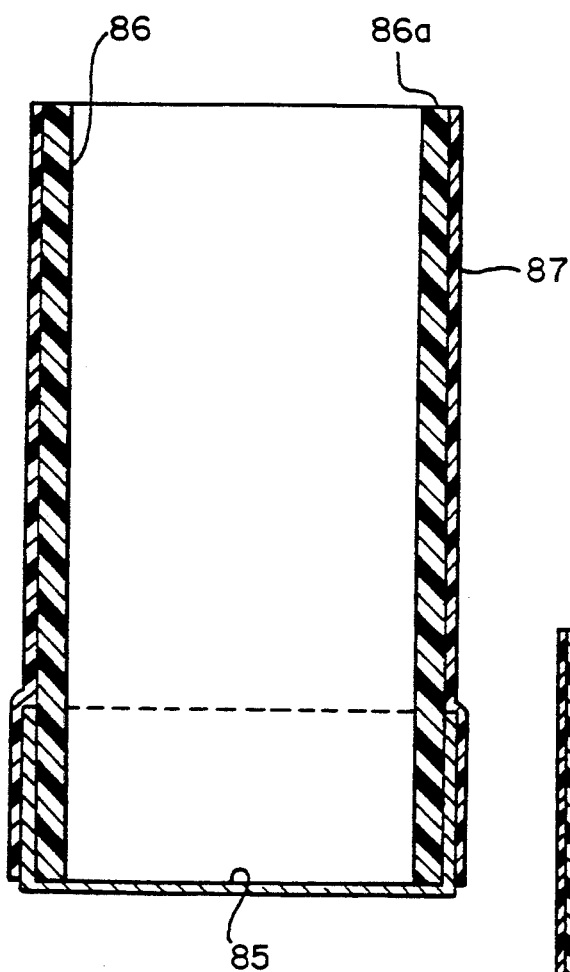
FIGS. 18A, B, C and D are views in vertical section of container assemblies illustrating another embodiment of the invention.

Referring to FIGS. 18A, B, C and D there is illustrated another embodiment of the invention which achieves features of both the single load embodiments of FIGS. 1–12 and the multiple load embodiments of FIGS. 13–17 as well as additional features of lower cost, reduced energy consumption and self-lidding of the processed container.

FIG. 18A illustrates a medical waste receiving and processing container 84 which includes a permanent heat-resistant housing part in the form of an open metal can 85 and a temporary or expendable hopper section 86 comprised for example of an extruded cylindrical sleeve formed of temperature-calibrated thermoplastic such as moldable grade polypropylene formulated to achieve full flow liquidity at approximately 190° to 200° C. The two components can be integrated by, for example, force-fitting or heat sealing. If desired the two can be united by a common heat-resistant film or foil lamination or a filamentary wrap 87 which can include graphics such as instructions, warnings, logos or the like and which can also function as a isolation layer to shield and support the softened or liquefied thermoplastic sleeve 86 as described below. It will be understood that the layer 87 can also be a sprayed-on resilient heat-resistant coating of latex. Pigments can be added to sleeve 86 to render it opaque.

The relationship of the volumes of the permanent housing part or can 85 and the hopper section 86 is critical to this embodiment of the invention, the former being the ultimate container for the fully processed waste in the form of a dense, sterile, void-free mass of encapsulating plastic and medical sharps. A one pint volume is thought to be generally suitable in weight and size for handling and disposal in the normal channels of domestic waste removal. This translates into a loading of unprocessed waste displacing a volume of approximately 1½ to 2 quarts (depending on load characteristics) and the hopper section can be so proportioned. Thus only a single melt-down cycle is required to achieve a full disposable volume of the processed waste, this in contrast to the embodiment of FIGS. 13–17 in which multiple melt-downs are proposed for filling the final container. The thickness of the sleeve 86 of thermoplastic can be selected to yield a volume of plastic which when melted down will fill approximately one-half of the can 85 to provide for the encapsulation of waste items which are lacking for the most part in any thermoplastic content. The thermoplastic sleeve thus performs the multiple functions of filling the void spaces among non-meltable items such as glass, guaranteeing sterilization by exposure of the surfaces to its critical liquefaction temperature and effecting a dramatic and highly visible change in the geometry of the processed container assembly i.e. the entire exposed portion of the hopper section disappears as the assembly contracts to about ⅓ to ¼ its original size. The sleeve 86 also performs the critical function of guiding the pre-processing compaction stroke of the oven as described below.

Figure 18B:
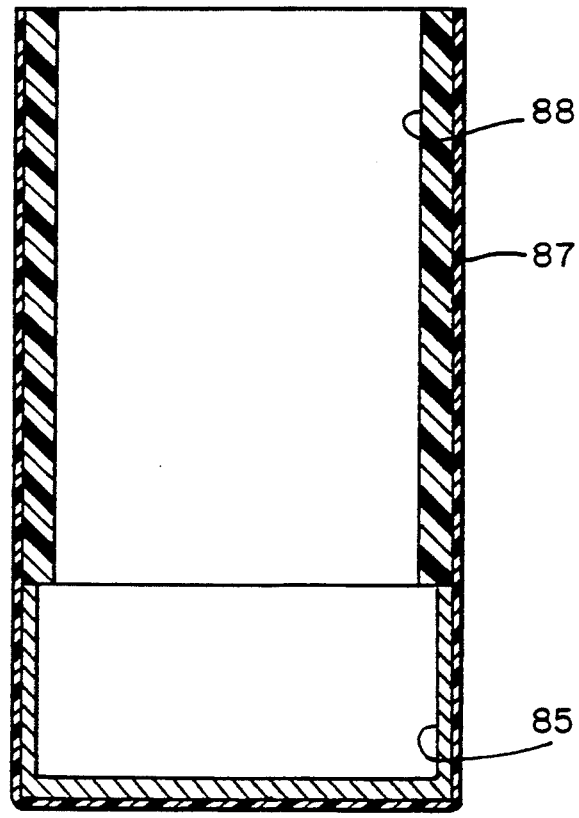
Figure 18C:
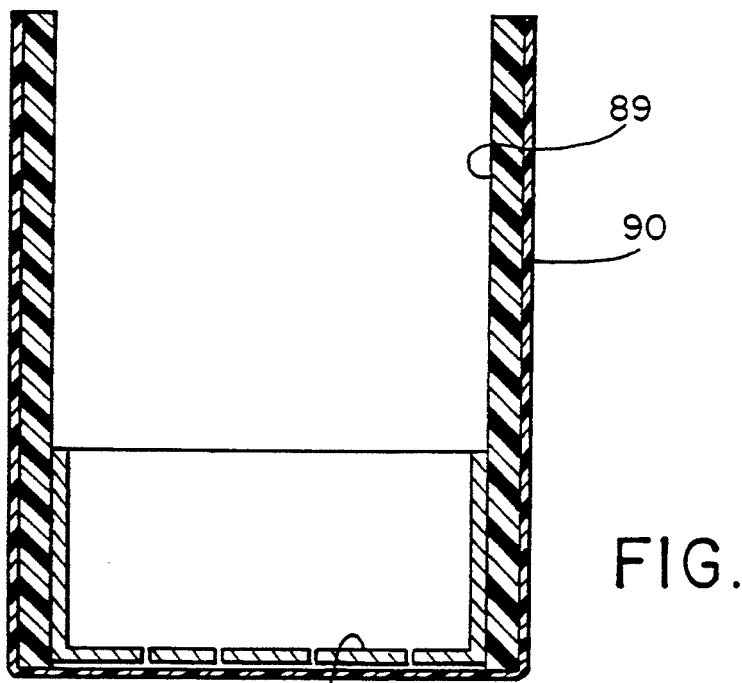

FIGS. 18B and C show variations of the design of FIG. 18A and in which like components are identified by like reference numerals. In FIGS. 18B the permanent heat-resistant housing part or can 85 is surmounted by a shortened hopper section sleeve 88, slightly larger in diameter and wall thickness than the sleeve 86 of FIG. 18A and joined to the upper edge only of the can 85. The assembly can be integrated by the thin foil, film or filamentary layer 87 to control the flow of the liquefied thermoplastic sleeve. In the arrangement of FIG. 18C the can 85 is surrounded by the lower end of a hopper sleeve 89 having a still larger i.d.. The assembly is completed by a thin walled, heat resistant outer plastic container 90 formed of polyethylene terephthalate and commonly known as PET, blow molded to yield surfaces which shrink under exposure to heat at the level contemplated by this invention on both the x and y axes. When subjected to processing heat in the oven, the PET softens and shrinks (but does not liquefy) driving the liquefied thermoplastic sleeve 89 upwardly over the lip of the can 85 and inwardly to gravitate downward into the can.

Figure 18D:
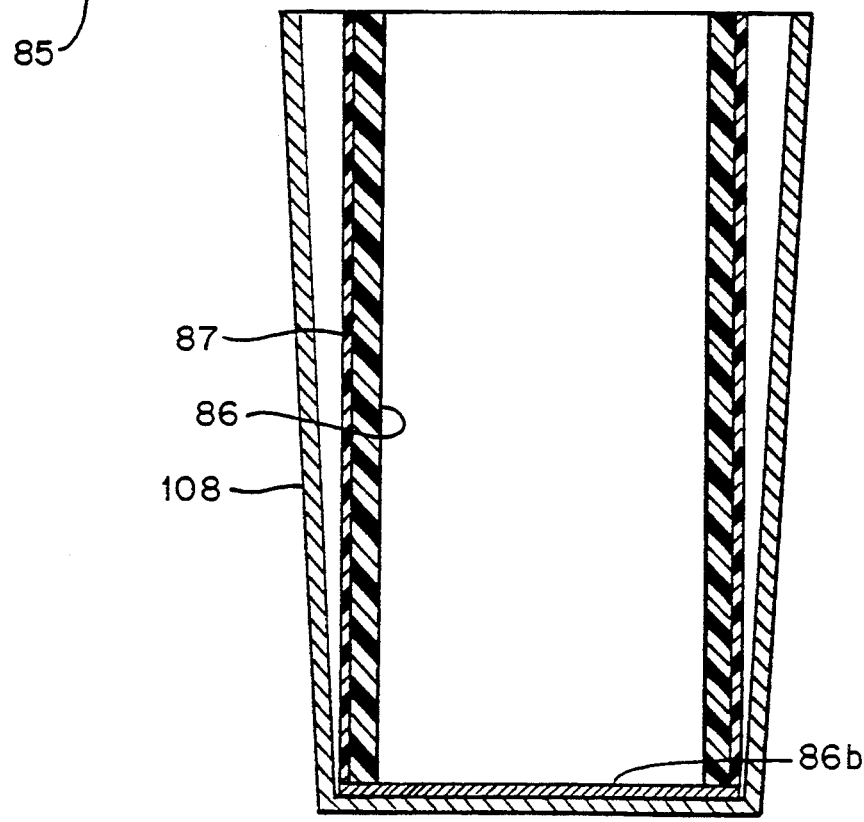

FIG. 18D illustrates principles of the embodiments of FIGS. 18A–C but as applied to the embodiments of FIGS. 11 and 12. The straight-walled cylindrical sleeve 86 contains an applied heat-resistant, resilient coating or lamination 87 and an applied bottom disk 86b which can be formed of a heavy paper board bearing, if desired, legends, instructions and certification labelling. The sleeve is seated in a supplemental container 108 (FIGS. 19, 20, 21, 22 and 23 and described in greater detail in conjunction therewith). The permanent heat resistant housing part 85 of FIGS. 18A–C and which survives the heat processing step and becomes part of the final package to be discarded in the conventional channels of waste disposal is replaced by the supplemental container 108 which serves as the processing container only. The expendable cylindrical sleeve 86 accommodates and implements the pre-processing waste compaction cycle (as described below) and in conjunction with its lamination 87 undergoes the melt-down and total sterilizing cycle which includes final compaction into a void free structure as well as self-lidding.

Figure 19:
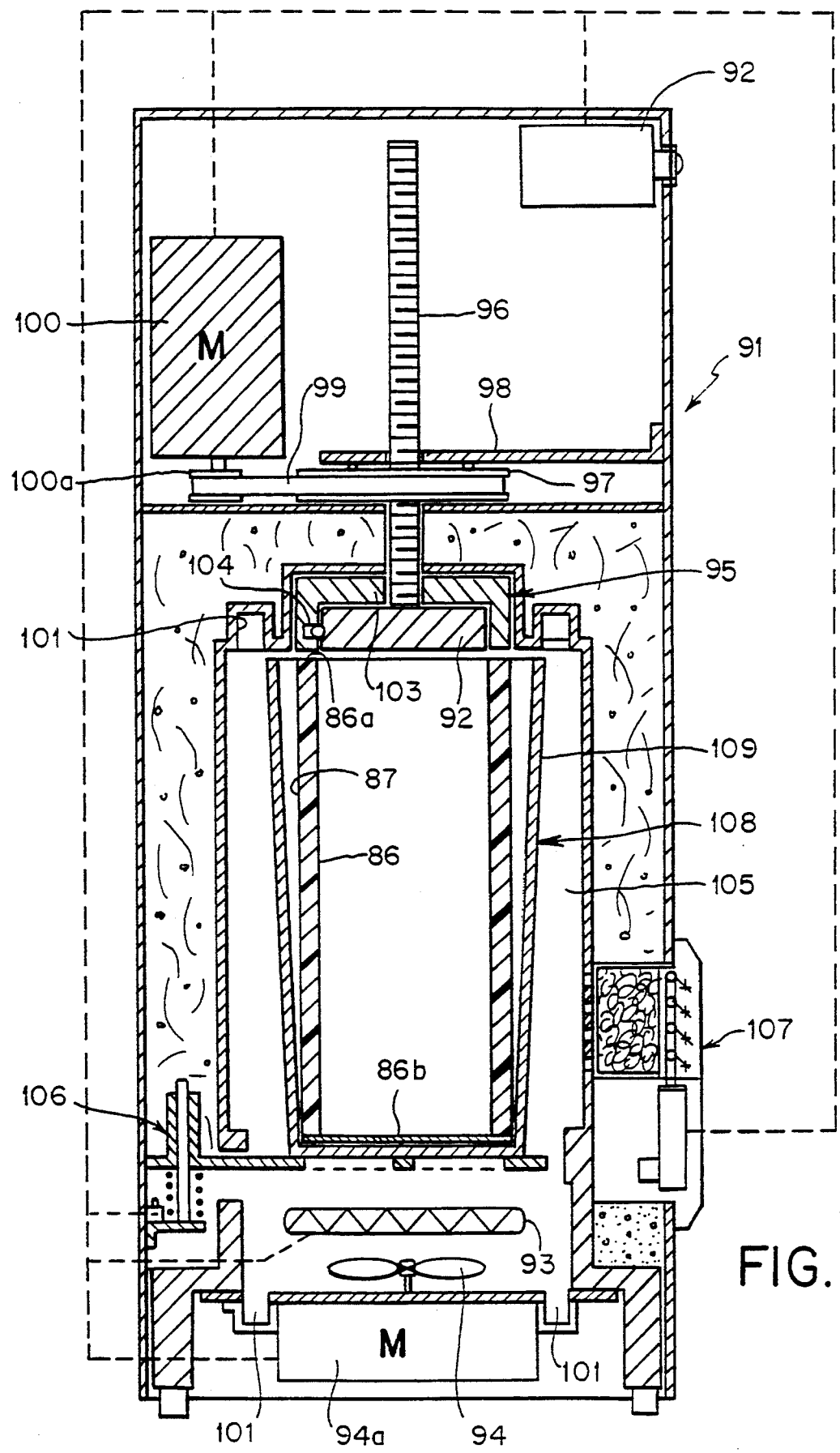
FIG. 19 is a side view in vertical section taken on the line 19A—19A of FIG. 21 of an oven for processing the container assembly of FIGS. 18A–D.

Referring to FIG. 19 there is shown, partly in schematic form, a processing oven 91 including a thermostat, timer and processing control 92 which can be programmed to carry out a desired sequence of operations including preliminary heating (below the temperature of melt down of the hopper section 86 of the container assemblies), preliminary compaction of the waste load (described in greater detail below), a full melt down cycle and the final self-lidding or container sealing operation. The processing control 92 is shown connected diagrammatically by broken lines to the several functioning elements of the oven.

The oven 91 includes an electrical resistance heater element 93 and an air circulating fan 94 and fan motor 94a to establish convection currents for controlled heating and cooling. Vertical ducts 101 couple the upper end of the oven to the return side of the fan 94. A power driven compactor 95 including a piston drive screw 96 driven by an internally-threaded, large pulley 97 held by thrust bearing 98 and driven by a belt 99 from a small driver pulley 100a coupled to a reversible motor 100. The working end of the compactor includes a central piston 102 sized to fit within the sleeve 86 of the hopper section of the waste container assembly 84 and a weighted concentric outer rim portion 103 coupled by a pressure releasable detent 104 to the central piston 102 and otherwise free of the drive screw 96 for relative axial movement. The rim portion 103 is sized to rest on the upper edge 86a of the hopper section 86 to control as needed the self-lidding action of the container assembly 84. The sleeve 86 is of uniform cross-sectional size and geometry along at least its upper portions to accommodate the piston 102.

The oven 91 includes a heating space 105 defined by an insulated semi-circular wall 105a to receive the container assembly for processing and a load-weighing scale 106. The scale reorganizes the weight but not the volume of the medical waste and therefore can sense both the loading of raw waste and melted down waste as well as crushed or uncrushed glass waste for compression with a predetermined maximum load weight. It is, therefore, possible in accordance with the invention to preliminarily process medical waste by melting down or compressing less than total capacity waste loads into the permanent housing part 85 while continuing to accumulate unprocessed waste in the hopper section 86. When the aggregated weight reaches the value of the predetermined weight of a void-free mass filling or capable of filling the can part 85 a signal can be obtained from the apparatus which will end the process by calling for a final melt-down which will not overfill the can. The automatic scale can also be used to tune the system to receive loadings of waste which differ significantly from routine medical wastes.

Daily treating of medical waste is required by certain jurisdictions. The system can, therefore, be activated within each of such periods to air-sterilize the waste by heating to a point below liquefaction of the master sleeve 86 but for a sufficient time interval to effect evaporation of ambient residue liquids and almost if not complete sterilization prior to the final and conclusive melt-down and sterilization cycle. Conventional hot air sterilization (regarded as total) can be achieved by a 60 minute cycle at 150° C.

Referring to FIGS. 22 and 23 the available action and functions of the compactor 95 are illustrated. FIG. 22 shows the piston 102 at the conclusion a compaction cycle in which a full load of waste such for example as unbroken glass vials, thermoplastic syringes and randomly disposed needles has been pressed downward into the can 85, breaking the glass, flattening the syringes and disposing any upwardly extending needles horizontally. It is preferred that this piston stroke be performed after a pre-heating cycle of up to 30 minutes at approximately 150° C. has been carried out to dry any residual moisture in the load, to soften the thermoplastic syringe bodies and to at least partially air sterilize the mass. The inner piston 102, being cylindrical and closely matched to the i.d. of the sleeve 86 has entered the sleeve. The outer, weighted rim 105 of the piston has engaged the upper and still rigid edge of the hopper section sleeve 86 and broken the detent coupling 104 with the central piston 102 allowing it to descend to compress the waste load. The travel of the piston can be limited to the top edge of the can 85, if used, and can be additionally controlled in its travel by a compacting pressure limit on the order of say 50 to 80 psi. It will be understood that this pre-melt down compaction stroke is essential for loadings for example of glass vials but can be omitted for loading which are mostly thermoplastic.

At the completion of the down stroke, the piston is withdrawn and a melt-down heating cycle begun in which the oven temperature is raised to approximately 190° to 200° C. The compacted waste load, to the extent it contains thermoplastic, will liquefy and the sleeve 86 of the hopper section will soften and then liquefy to begin gravitating downward into and over the waste mass. At the conclusion of the melt-down cycle of say to 30 to 50 minutes the entire mass heated to at least 190° to 200° C., will be rendered verifiably sterile.

The geometry of container assembly at this point will depend on the selection of the heat resistant outer layer 87. A film, foil or filamentary wrap holding on its inner surface only a residue of the melted down sleeve 86 can hold or at least partially hold the integrity of the structure. While in certain cases the outer layer might protect the piston against engaging liquefied plastic, the problem, if it exists, can be avoided by a brief cooling cycle with the fan 94 operating and if desired, a vent door or louver and filter assembly 107 in the oven opened by the controller 92 to lower the temperature of the plastic mass to at least partially solidify the temperature-calibrated plastic at which time the controller 92 lowers the compactor piston 102-103 to engage the upstanding container structure.

The piston will function as a heat sink to insure a partially hardened skin or layer of plastic beneath it and will cause the container to be self-lidding as the hardened skin presses down on the relatively soft mass to form the finished processed container. Piston pressure of 50 to 80 psi assures the absence of significant voids in the mass. The outer piston ring 103 will yield at the point of engagement with the lamination 87 overlying the upper edge of the can 85, if used, allowing the piston, should the load be somewhat less than the full capacity of the can 85 to insure full compaction of the load. A lamination 87 in the form of a resilient, heat-resistant latex will function in the heat to guide the sleeve gently inward.

Figure 20:
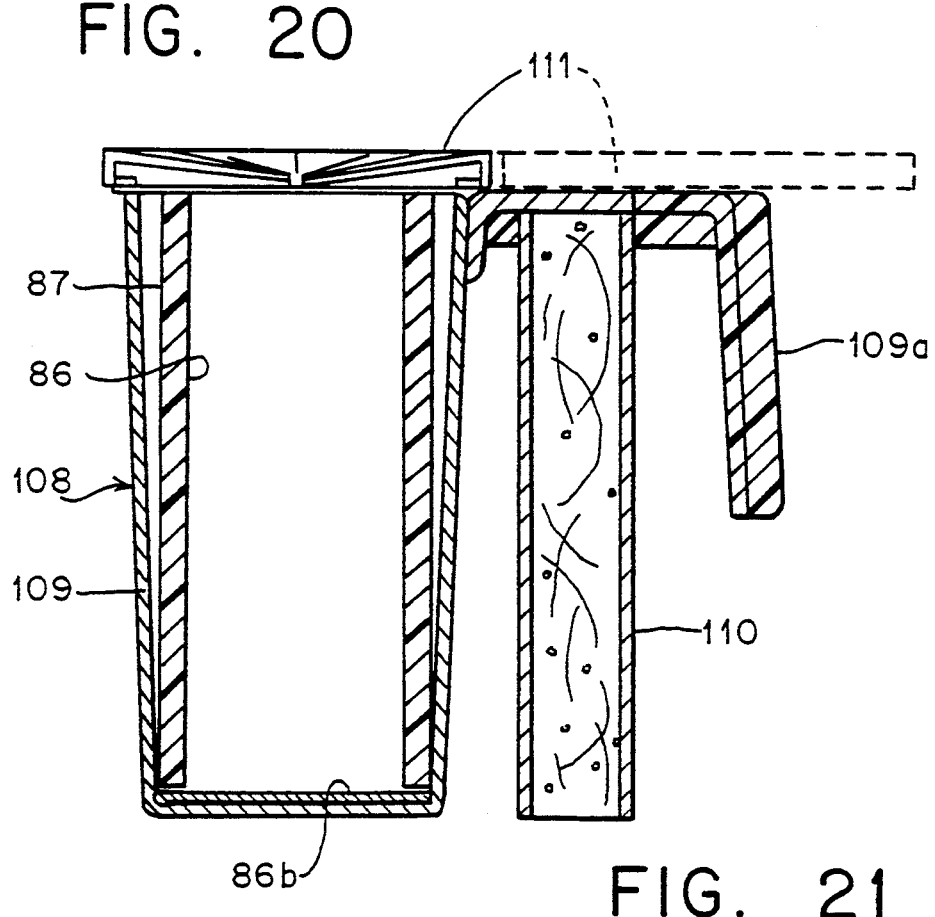
FIGS. 20 and 21 are, respectively, views in vertical and horizontal section of a supplemental carrying container for the container assemblies of FIGS. 18A-D and showing also fragments of the oven of FIG. 19 and the integration of the supplemental carrying container and the oven.
Figure 21:
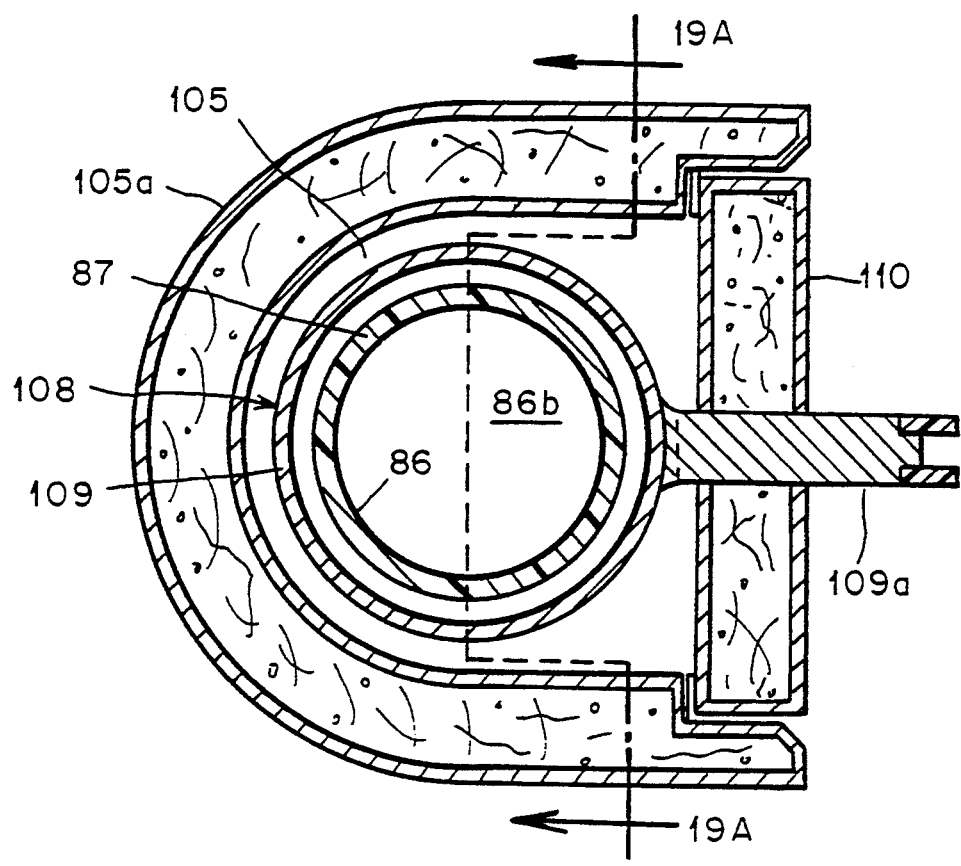

Referring to FIGS. 20 and 21 there is shown a receptacle 108 comprising an inner cylindrical sleeve 109 tapered gently inward from the top and dimensioned to receive the container assemblies of FIGS. 18A-D for both filling and processing. An insulated face piece 110, a handle 109A and a slidable lid 111 complete the receptacle assembly. The oven space 105 is contoured to receive the receptacle 108, with the face piece 110 functioning as a door to close the opening on the oven wall. The lid 111 will slide back automatically. The receptacle 108, if used, can also function as a holder at the point of use.

The receptacle 108 or its equivalent is required for the embodiment of FIG. 18D and functions not only as a carrier but as a melt down container taking over a function of the can 85. The sleeve 109, being tapered will allow the processed hardened contracted waste mass (FIG. 21) to release easily from the receptacle to be deposited in a conventional waste receptacle. Teflon or other durable parting agent can be used, if needed, on the inner walls. The certification legends and other information imprinted on the bottom of the base cover 86b will be clearly visible on the discarded piece.

In the event a compactor is not incorporated in the oven the self-lidding and at least some compression of the container assembles can be achieved by a compression spring, (similar to the spring 21 of FIGS. 9 and 10) in the sleeve 109 adapted to be compressed manually when the container assembly is inserted therein. If desired, a hold down latch can be incorporated in the receptacle and activation (not shown) can be provided in the oven under the control of the sequence controller unit 92.

Figure 24:
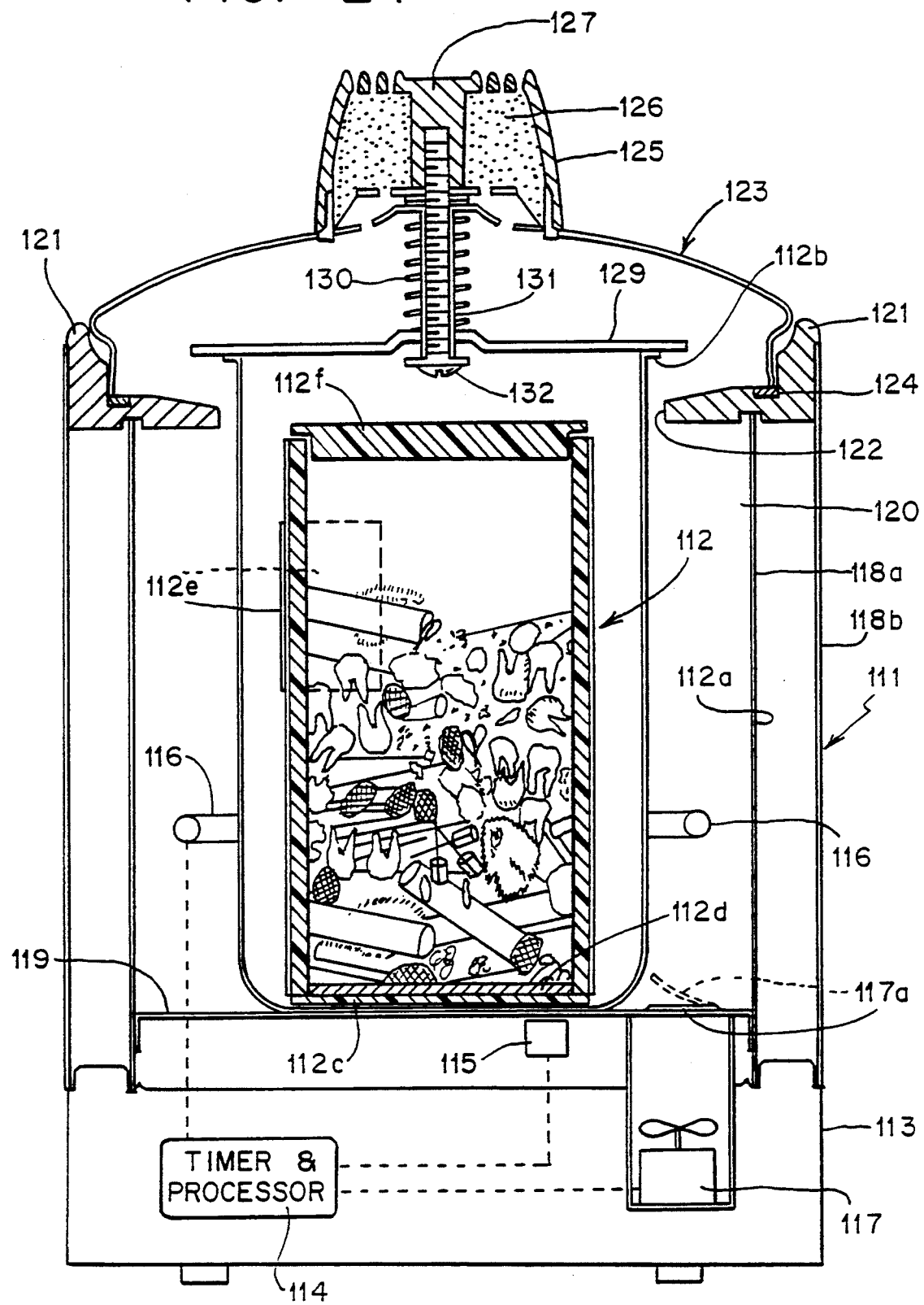
FIG. 24 is a view in vertical cross section of a processing oven incorporating fume and vapor controls and showing a processing receptacle containing an expendable plastic container filled with unprocessed medical waste.
Figure 25:
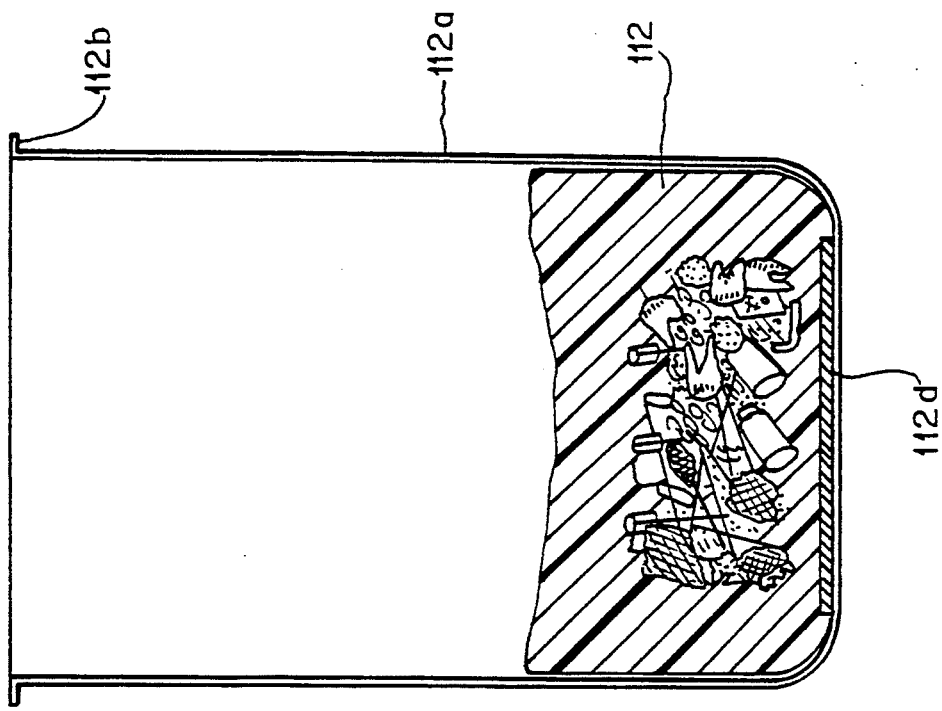
FIGS. 25 and 26 show in vertical cross sections, respectively, the receptacles containing the waste load during processing and at the conclusion of processing.
Figure 26:
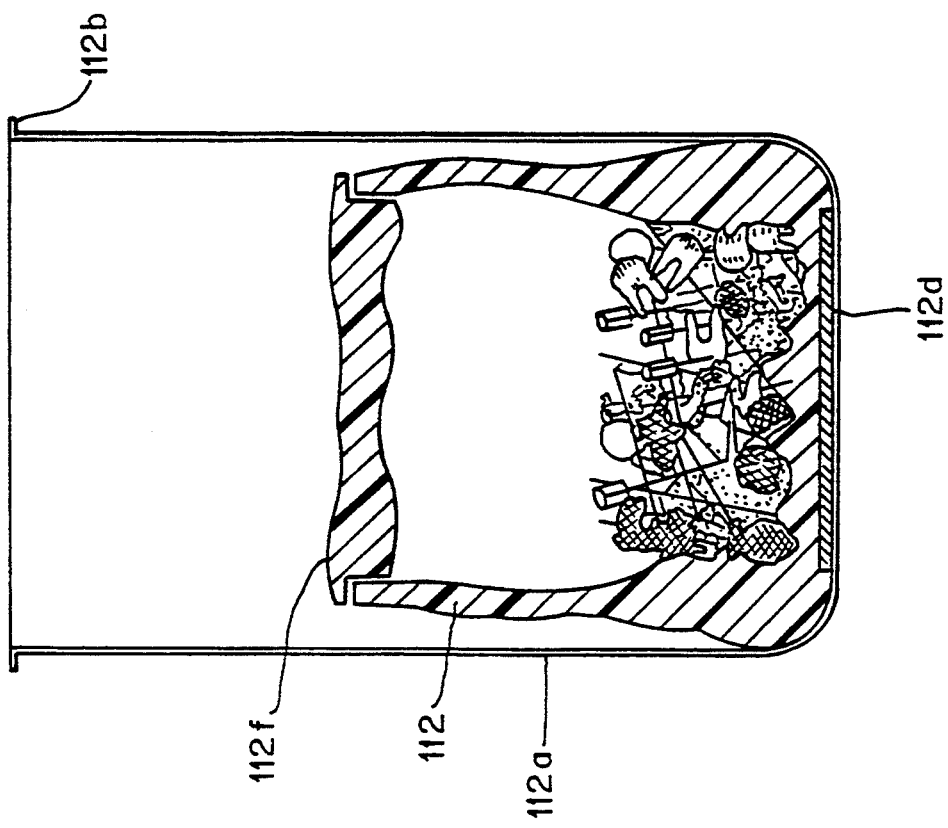

Referring to FIGS. 24-26, there are disclosed an oven-processor 111 and, seated therein for processing a self-lidding, expendable coated waste container 112. The container is shown filled with an assortment of medical waste sharps. As in the case of other species of the invention described above, the container 112 is received in a processing receptacle 112a, preferably formed of metal and Teflon lined.

The processor 111 includes a base 113 (illustrated diagrammatically) containing a timer and processing control circuit 114 operatively connected to a temperature sensor 115 critically placed beneath the load, a heating coil 116, also critically placed proximate the lower end of the load, and a cooling fan used for speeding the completion of the processing cycle. Double cylindrical side walls 118a and 118b supported by the base provide insulation and define, together with a bottom plate 119, an internal processing space 120. A contoured, annular top rib 121 carried by the walls is formed with a circular opening 122 through which the unit is loaded. A flange 112b on the receptacle 112 facilitates handling during loading and unloading.

A removable cover 123 seats on the top rib 121 snugly upon a gasket 124. A cover lock (not shown) can be provided. A handling knob 125 containing venting apertures and a replaceable filtering medium 126 is affixed to the cover. A depending boss 127 in the knob carries a perforated plate for the filter and a centrally pierced, vapor sealing disk 129 which rests on the upper flange of 112b of the processing receptacle 112a under the light pressure of a compression spring 130 surrounding a sleeve 131, all secured by a mounting screw 132.

The processing receptacle 112a is generally similar to that of FIG. 18D as is the expendable waste container 112 which includes a plastic bottom 112C and a non-meltable insert label 112d resting on the bottom. The insert label 112d carries downwardly facing labelling which is not visible before processing but which sinks in the molten plastic under the weight above it so that it becomes visible in final processed mass to become a visible verifier of the sterilizing process. A self-destroying label 112e formed, for example, of plastic which shrinks or melts or both during processing is affixed to the side wall of the container 112. This label identifies the waste as being regulated or dangerous in the manner that all conventional sharps containers are labelled.

As in the containers of FIGS. 18A–D, the side walls of the containers can be coated with a laminate of plastic having higher heat resistance than the body to help control the collapsing action of the unit during melt down. In addition to the methods of lamination disclosed above in connection with FIGS. 18A–D, the control coating or lamination can be applied by co-extrusion at the time the body portion is being formed by the extrusion process. Also as described above referring to FIGS. 12 and 18–23, self-lidding of the expendable waste container is possible without need for a discrete non-meltable lid which becomes part of the throw-away unit. Processing of the units having no discrete lid elements relied at least to some extent on external elements which were part of the processing oven such as springs, drive screws, non-adhering gravity driven elements and the like. Moreover, reduction of the final unit to a void-free structure and assurance that the molten plastic reached all contaminated surfaces of the waste was augmented by such techniques.

In the species of the invention disclosed in FIGS. 24–26, however, self-lidding and compaction of the mass, when necessary, is achieved by an expendable lid 112f which is seated on the container 112 after is loaded. This lid is self-weighted by its own mass and is illustrated in FIG. 24 as a relatively thick disc of thermoplastic. It can be of the same material as the side walls or if desired, of a material having a slightly higher melting point. Its mass affords compaction forces and also assures sufficient plastic to cover and seal extraneous waste items.

It will also be seen in FIG. 24 that the heating element 116 and the temperature sensor 115 of the processing oven are critically located in the lower parts of the processing oven. When the sterilizing and encapsulating process begins, heat is concentrated in precisely regulated amounts at the lower end of the waste mass. Referring to FIG. 25, the container and its mass of waste are illustrated at an intermediate stage in the processing cycle, with melting occurring at the bottom while the self-weighted upper portion slowly lowers with out disintegration of the unitary structure above. The lid portion 112f is shown softened but generally integrated to supply gentle downward pressure as the side walls melt into the mass below. In FIG. 26, the lid portion has melted and the waste has been fully processed including a cooling cycle in which the fan 117 was actuated, opening the flapper valve 117a and establishing a flow of cooling air upward around the receptacle 112a and out of the processing oven through the aperture 122 and out of the lid 123 through the filter 126. If desired cooling can be augmented by vents (not shown) in the disk 129 and the lid 123 operated, for example, by bi-metal controls.

It will be observed that the cooling process caused contraction of the compacted waste mass helping to break it free of the Teflon lined receptacle. The danger warning label 112e has disappeared and the identifying insert label 112d has become visible. The action of the heat sensor and heating element holds the temperature throughout processing at levels achieving liquefaction of the temperature-calibrated thermoplastic but below vaporization and gassing-off temperatures. To the extent that gases might be generated within the waste mass, particularly early in the processing cycle, they are contained by the disc 129 bearing on the lip of the receptacle 112a. Small bursts of gas escaping this yieldable barrier are largely condensed on the relatively cool inner surfaces of the lid structure and any gas leaving the unit passes through the filter 126. Thus, on-site processing of sharps into non-regulated waste can be accomplished safely, without extraneous odors. The processed sterile mass which has been rendered "unregulated", can be easily removed from the receptacle 112a and discarded.

While the invention has been described having reference to preferred embodiments it will be understood that it can take other forms and arrangements. For example, the temperature-calibrated element can be formed of materials other than plastic, so long as the material in its molten state is compatible with the temperatures required in the time/temperature death rate curve and has appropriate liquid and solid phases. It is also important that the molten material be brought into intimate contact with the contaminated waste material. In addition to the preferred embodiments herein disclosed it will be understood that this encapsulation can be augmented by rolling, tumbling, shaking, vibrating, and air evacuation devices. Partial evacuation of the container can perform the manifold functions of aspirating waste gases, augmenting the flow of the liquid-phase plastic into all voids and of providing some or even all of the compression forces to cause the distortion of the container. This distortion forces the liquid into the mass of waste implements and, at the same time, provides for the easily viewed indication of successful completion of the sterilizing cycle. In the preferred embodiments the essential operational functions have been divided between the oven and the container. For example, the oven is the source of the controlled heat as well as the pressure, i.e. the spring 21, or compactor 95 to extrude the liquefied sterilizing medium into the mass of waste pieces. As disclosed, some or all of this pressure can be generated solely within the container itself by, for example, the internal spring 37 (FIGS. 5 and 6), the resilience of the base 18 (FIGS. 1–4) or the heat shrinking forces of certain plastics. It will be understood that it is possible to generate heat by different means such as chemically within the container itself or by means of microwave energy focussed on the solid plastic, avoiding to the extent possible solid metal items. The plastic can be rendered more susceptible to such heating by means of carbon dielectric fillers. It is also possible to establish more of the functions externally of the container by, for example, generating the liquefied sterilizing medium externally and injecting it into the waste filled containers, which can be partially evacuated to augment the liquid flow to create a void-free mass and which can also provide a force to deform the container to provide a visual indication that the process has been completed. The invention should not, therefore, be regarded as limited except as defined in the following claims.

I claim:

1. A self-lidding thermoplastic container for receiving regulated medical waste and for facilitating verifiable thermal processing of the waste into non-regulated form for disposal, comprising:

an expendable container for receiving the waste and formed at least in part of temperature-calibrated thermoplastic having a liquefaction temperature which achieves sterilization substantially within the time frame of liquefaction and re-solidification, and a thermoplastic cover for the container having a substantial mass to impart compression to the container during liquefaction and to impart supplemental thermoplastic mass for augmenting encapsulation of the waste and the formation of a unified sterile mass for disposal.

2. A container as set forth in claim 1, said container including substantially tubular thermoplastic walls, and a laminate of thermoplastic material on said walls and having higher thermal resistance to impart control to the walls during liquefaction.

3. A container as set forth in claim 1, including a thermoplastic bottom portion on the container and an indicia-bearing heat-resistant label on the bottom portion adapted to sink during processing into the bottom portion to become visible after processing.

4. In combination, the container as set forth in claim 1, including an oven-processor for receiving the container including means for sensing the temperature of the base of the container during processing, and means for directing oven heat to the lower portion of the container during processing under the control of the sensing means.

5. The combination set forth in claim 4, including a heat resistant receptacle for receiving said container for processing in the oven-processor, and a yieldable cover member in said oven-processor for covering the receptacle during processing and yieldable under internal pressure to controllably vent gases from the waste.

6. An expendable thermoplastic container for receiving medical waste and for facilitating verifiable thermal processing of the waste into form for disposal, comprising:

a body portion including a substantially tubular side wall formed of temperature-calibrated thermoplastic adapted to liquefy at a temperature achieving sterilization within the time frame of liquefaction and re-solidification, and a lamination on said tubular wall selected from among films and foils having thermal resistance exceeding that of the wall to control the flow of liquefied plastic.

7. A container as set forth in claim 6, in which the tubular wall and its laminate are co-extruded.

8. A container as set forth in claim 6, including a heat-resistant receptacle for receiving said container and adapted to function as a mold for the molten mass.

9. A container as set forth in claim 8, said receptacle comprising an element of the processed mass to be disposed of therewith.

10. A container as set forth in claim 8, said receptacle comprising a permanent fixture adapted to receive successive waste containers for processing.

11. An oven assembly for processing regulated medical waste in situ comprising a waste treatment space for receiving the waste in conjunction with a mass of temperature calibrated thermoplastic, means to provide processing heat selectively in at least two different processing temperature ranges one of which is below the temperature of liquefaction of the thermoplastic and one of which is at or above the temperature of liquefaction, and timer means to control the duration of each processing operation.

12. An oven assembly as set forth in claim 11 including compression means for the waste and selectively operable means for the compression means.

13. An oven assembly as set forth in claim 11 including a heat resistant container for receiving the medical waste and thermoplastic in the form of a sleeve member defining a waste-receiving hopper and functioning as a permanent housing part for the waste and thermoplastic throughout the processing operation.

14. Apparatus as set forth in claim 13 said compression means including a piston means adapted to engage the waste in the hopper and means to drive the piston into the waste prior to and after liquefaction of the thermoplastic sleeve.

15. Apparatus as set forth in claim 14 said piston means including a first part to enter the thermoplastic sleeve and a second part to engage the sleeve member, said first and second piston parts being relatively movable.

16. Apparatus as set forth in claim 11 said means to provide heat being selectively operable at a first temperature to dry and soften the medical waste for compaction and at a second temperature to melt down the thermoplastic to form a substantially void free mass in the permanent housing part.

17. Apparatus as set forth in claim 11 including fan means in the oven to circulate air to the waste at selected temperatures ranging from external ambient to cool the container to solidify the load, to intermediate temperatures to soften the load for drying and compaction and to maximum temperature for liquefaction of the temperature calibrated thermoplastic.

18. Apparatus as set forth in claim 13 said mass of temperature calibrated thermoplastic being formed into a storage hopper holding the medical waste, said oven including scale means to weigh the waste and thermoplastic and means responsive to the scale means to indicate the storage hopper is filled to the volumetric capacity of the permanent housing part to hold processed medical waste.

19. A method for heat-processing regulated medical waste selected from among breakable, compressible, thermoplastic and metallic items, the steps of a) accumulating the waste items in a container formed at least in part of temperature calibrated thermoplastic, b) applying pressure to waste items within the container to reduce the volume thereof while maintaining a temperature below liquefaction of the thermoplastic, c) heating the container and reduced waste volume to at least the temperature of liquefaction of the temperature calibrated thermoplastic, d) collecting the waste and liquefied thermoplastic in a heat and pressure resistant container while applying pressure to the mass to form a void-free plastic impregnated and encased mass, and e) hardening the mass to create a biologically sterile unitary mass in which all sharp edges and points are encapsulated against exposure.

* * * * *